United States Patent
Marshall et al.

(10) Patent No.: US 12,336,780 B2
(45) Date of Patent: Jun. 24, 2025

(54) SURGICAL DRAPE FOR TRANSFERRING DRIVE

(71) Applicant: CMR SURGICAL LIMITED, Cambridge (GB)

(72) Inventors: Keith Marshall, Cambridge (GB); Rebecca Anne Cuthbertson, Cambridge (GB); Nikki Priyam Su-Ling Phoolchund, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 470 days.

(21) Appl. No.: 15/572,098

(22) PCT Filed: May 6, 2016

(86) PCT No.: PCT/GB2016/051303
§ 371 (c)(1),
(2) Date: Nov. 6, 2017

(87) PCT Pub. No.: WO2016/178028
PCT Pub. Date: Nov. 10, 2016

(65) Prior Publication Data
US 2018/0132959 A1 May 17, 2018

(30) Foreign Application Priority Data

| May 7, 2015 | (GB) | 1507804 |
| May 7, 2015 | (GB) | 1507805 |
| May 15, 2015 | (GB) | 1508445 |

(51) Int. Cl.
*A61B 46/10* (2016.01)
*A61B 34/00* (2016.01)
(Continued)

(52) U.S. Cl.
CPC .............. *A61B 46/10* (2016.02); *A61B 34/30* (2016.02); *A61B 34/71* (2016.02);
(Continued)

(58) Field of Classification Search
CPC ..... A61B 46/00; A61B 46/10; A61B 1/00135; A61B 1/00142; A61B 34/71; A61B 46/13;
(Continued)

(56) References Cited

U.S. PATENT DOCUMENTS 7,666,191 B2 * 2/2010 Orban, III .............. A61B 46/10
606/1
9,839,487 B2 * 12/2017 Dachs, II ............... A61B 90/98
(Continued)

FOREIGN PATENT DOCUMENTS

| CN | 101242789 | 8/2008 |
| CN | 104394793 A | 3/2015 |

(Continued)

OTHER PUBLICATIONS

Collins Dictionary, "interface," https://www.collinsdictionary.com/US/dictionary/english/interface.*
(Continued)

*Primary Examiner* — Victoria Hicks Fisher
(74) *Attorney, Agent, or Firm* — Renner, Otto, Boisselle & Sklar, LLP

(57) ABSTRACT

A surgical robotic drape for enveloping a portion of a surgical robot that comprises an instrument having at least one joint, and a robotic arm comprising a drive assembly configured to provide mechanical drive for selectively actuating the at least one joint, the instrument and drive assembly each having a plurality of interfaces for coupling mechanical drive from the drive assembly to the instrument, the drape comprising: a covering for enveloping the surgical
(Continued)

robot drive assembly to define a sterile boundary thereover; and a plurality of interface elements each configured to engage with both a drive assembly interface and an instrument interface to couple the drive assembly to the instrument to thereby transfer mechanical drive provided by the drive assembly through the drape to selectively actuate the at least one joint of the instrument, the plurality of interface elements being attached to the covering in a spatial arrangement so that each of the plurality of interface elements is separated from each of the other plurality of interface elements by material of the covering.

20 Claims, 14 Drawing Sheets

(51) Int. Cl.
    *A61B 34/30*     (2016.01)
    *B25J 19/00*     (2006.01)
    *A61B 17/00*     (2006.01)
    *A61B 46/00*     (2016.01)

(52) U.S. Cl.
    CPC . *B25J 19/0075* (2013.01); *A61B 2017/00477* (2013.01); *A61B 46/40* (2016.02)

(58) Field of Classification Search
    CPC ... A61B 46/17; A61B 46/20; A61B 2046/201; A61B 2046/205; A61B 46/23; A61B 2046/234; A61B 2046/236; A61B 46/27; A61B 46/30; A61B 46/40; B25J 19/0075
    See application file for complete search history.

(56) References Cited

U.S. PATENT DOCUMENTS

| | | |
|---|---|---|
| 2007/0043338 A1 | 2/2007 | Moll et al. |
| 2007/0137371 A1* | 6/2007 | Devengenzo .......... A61B 34/30 74/490.01 |
| 2009/0248039 A1 | 10/2009 | Cooper et al. |
| 2010/0170519 A1 | 7/2010 | Romo et al. |
| 2011/0277776 A1* | 11/2011 | McGrogan ......... A61B 17/3474 606/130 |
| 2012/0071752 A1 | 3/2012 | Sewell et al. |
| 2012/0289973 A1 | 11/2012 | Prisco et al. |
| 2012/0289974 A1 | 11/2012 | Rogers et al. |

FOREIGN PATENT DOCUMENTS

| | | |
|---|---|---|
| JP | 2013-530738 | 8/2013 |
| WO | 2009061915 | 5/2009 |
| WO | 2013015933 | 10/2013 |
| WO | 20140005689 | 1/2014 |
| WO | 2015142795 | 9/2015 |

OTHER PUBLICATIONS

International Search Report regarding PCT/GB2016/051302, dated Feb. 8, 2016 (6pgs.).
Search report for related British application GB1508445.2, dated Oct. 29, 2017 (3 pgs.).
Search report for related British application GB1507805.8, dated Oct. 28, 2017 (4 pgs.).
International Search Report regarding PCT/GB2016/051303, dated Feb. 8, 2016 (5pgs.).
Written Opinion of the International Searching Authority related to PCT/GB2016/051302, dated Feb. 8, 2016 (7 pgs.).
Written Opinion of the International Searching Authority related to PCT/GB2016/051303, dated Feb. 8, 2016 (7 pgs.).
English language translation of Office Action of Chinese Application No. 201680026310.8, dated Nov. 11, 2019.
Notice of Reasons of Refusal for corresponding Japanese patent application No. 2017-557934 mailed on Feb. 10, 2020.
Notification of Reasons for Refusal dispatched Sep. 27, 2021, for corresponding Korean Patent Application No. 2020-186133.

* cited by examiner

SURGICAL DRAPE FOR TRANSFERRING DRIVE

BACKGROUND

This invention relates to a surgical drape comprising a plurality of interface elements for interfacing with a surgical instrument used during robotic surgery.

FIG. 1 shows a typical surgical robot for performing robotic surgery. The surgical robot 101 comprises a robotic arm 103 attached at one of its ends to a surgical instrument 105. The surgical instrument is operable to pass into a patient for performing surgery. The robotic arm comprises one or more joints 107 about which the arm can be articulated to control the movement and/or position of the surgical instrument. The robotic arm 103 is shrouded by a surgical drape 109 to provide a sterile boundary between the surgical instrument (which must be sterile) and the robotic arm (which may not be sterile). The drape provides a boundary between the robotic arm and the sterile field in which the arm is positioned (for example an operating theatre).

The surgical instrument may have one or more motional degrees of freedom. For example, the instrument may comprise a wrist joint and/or a distal end effector such as grippers or jaws. The wrist joint and end effectors may be capable of being articulated to enable the robot to perform certain steps of a surgical procedure. These articulations may be mechanically driven by a drive assembly powered by one or more motors. It is often desirable to house the drive assembly within the robotic arm rather than in the instrument. This is because the surgical instruments are subject to sterilisation which may damage the drive assembly. In addition, removing the drive assembly from the instrument reduces the cost of the instrument which may be desirable if the instrument was designed to be replaced after each surgical procedure.

Thus if the drive assembly is housed within the robotic arm, the mechanical drive needs to be connected, or coupled, to the instrument through the surgical drape. One way to do this is through the use of an interface plate. Such an interface plate typically comprises one or more plates (e.g. a front plate and a back plate) that retain a number of moveable interface elements. These interface elements couple to the drive assembly and the instrument to transfer the mechanical drive provided by the drive assembly to the instrument in order to drive the articulations of the instrument. The interface plate may be built into the drape, for example by perforating the drape and inserting the plate into the created opening. The drape can then be placed over the robotic arm and the interface place connected to the drive assembly. The instrument can then be connected to the interface plate, thus maintaining the sterile boundary.

A problem with the interface plate is that due to its relative complexity and number of parts, they can be relatively expensive to manufacture (compared to a surgical drape). Because the plate may also contain a number of interfacing elements, the plate may also be relatively bulky, making it more difficult to package and store the drape in a spatially effective way.

There is therefore a need for an improved surgical drape.

SUMMARY

According to one aspect of the present disclosure there is provided a surgical robotic drape for enveloping a portion of a surgical robot that comprises an instrument having at least one joint, and a robotic arm comprising a drive assembly configured to provide mechanical drive for selectively actuating the at least one joint, the instrument and drive assembly each having a plurality of interfaces for coupling mechanical drive from the drive assembly to the instrument, the drape comprising: a covering for enveloping the surgical robot drive assembly to define a sterile boundary thereover; and a plurality of interface elements each configured to engage with both a drive assembly interface and an instrument interface to couple the drive assembly to the instrument to thereby transfer mechanical drive provided by the drive assembly through the drape to selectively actuate the at least one joint of the instrument, the plurality of interface elements being attached to the covering in a spatial arrangement so that each of the plurality of interface elements is separated from each of the other plurality of interface elements by material of the covering.

The material of the covering may be flexible thereby causing each of the plurality of interface elements to not be fixed spatially relative to each of the other interface elements.

The material of the covering may be flexible thereby permitting the spatial arrangement of the interface elements to be adjusted.

The material of the covering may be flexible thereby permitting relative spatial movement between the plurality of interface elements to alter the spatial arrangement thereof.

The spatial arrangement of the interface elements with respect to each other may be dependent on the configuration of the covering.

Each interface element may comprise a first interfacing surface to engage a drive assembly interface and a second interfacing surface to engage an instrument interface.

Each of the plurality of interface elements may be configured to releasably engage with a drive assembly and instrument interface.

Each interface element may be configured so that its first interfacing surface is configured to engage a complementary surface of a drive assembly interface and its second interfacing surface is configured to engage a complementary surface of an instrument interface so that it requires a greater force to disengage the interface element from the drive assembly interface than from the instrument interface.

At least one of the plurality of interface elements may be configured so that its first interfacing surface comprises surface features configured to engage a complementary surface of a drive assembly interface.

At least one of the plurality of interface elements may be configured so that its second interfacing surface comprises surface features configured to engage a complementary surface of an instrument interface.

At least one of the plurality of interface elements may be configured so that its first interfacing surface comprises surface features configured to engage a complementary surface of a drive assembly interface and its second interfacing surface comprises surface features configured to engage a complementary surface of an instrument interface.

The surface features of the first interfacing surface may be configured to mate with a complementary surface of a drive assembly interface to thereby secure the drape to the robotic arm.

At least one of the plurality of interface elements may be configured so that its first interfacing surface comprises surface features in the form of a plurality of projections or plurality of recesses configured to engage a complementary surface of a drive assembly interface, and its second interfacing surface comprises surface features in the form of a plurality of projections or plurality of recesses configured to engage a complementary surface of an instrument interface.

The said at least one interface element may be configured so that its first interfacing surface comprises a greater number of projections or recesses than the corresponding number of projections or recesses on its second interfacing surface so that it requires a greater force to disengage said interface element from the drive assembly interface than from the instrument interface.

At least one of the plurality of interface elements may be configured so that its first interfacing surface comprises magnetic material, said first interfacing surface being configured to engage a drive assembly interface via magnetic attraction.

At least one of the plurality of interface elements may be configured so that its second interfacing surface comprises magnetic material, said second interfacing surface being configured to engage an instrument interface via magnetic attraction.

At least one of the plurality of interface elements may be configured so that its first interfacing surface comprises magnetic material, the first interfacing surface being configured to engage a drive assembly interface via magnetic attraction, and its second interfacing surface comprises magnetic material, the second interfacing surface being configured to engage an instrument interface via magnetic attraction, said first and second interfacing surfaces being configured so that the first interfacing surface engages the drive assembly interface with a stronger magnetic attraction than that with which the second interfacing surface engages the instrument interface.

The first interfacing surface of said at least one of the plurality of interface elements may comprise a guide slot configured to receive a lug that forms part of a drive assembly interface.

The second interfacing surface of said at least one of the plurality of interface elements may comprise a guide slot configured to receive a lug that forms part of an instrument interface.

At least one of the plurality of interface elements may be configured so that its first and second interfacing surfaces can rotate relative to surrounding material of the covering to transfer rotational drive from the drive assembly to the instrument to selectively actuate the at least one joint of the instrument, said at least one interface element being configured so that rotation of the first interfacing surface is coupled to rotation of the second interfacing surface.

At least one of the plurality of interface elements may be configured to engage the drive assembly interface and instrument interface to transfer linear drive of the drive assembly to the instrument to selectively actuate the at least one joint of the instrument.

At least one of the plurality of interface elements may be configured: (i) so that its first and second interfacing surfaces can rotate relative to surrounding material of the covering to transfer rotational drive from the drive assembly to the instrument to actuate a first joint of the instrument, said at least one interface element being configured so that rotation of the first interfacing surface is coupled to rotation of the second interfacing surface; and (ii) to engage the drive assembly interface and instrument interface to transfer linear drive from the drive assembly to the instrument to actuate a second joint of the instrument.

Each interface element may mounted directly to the covering.

Each interface element may be retained in place by the material of the covering.

Each interface element may be push-fitted onto the covering to attach the element thereto.

The plurality of interface elements may comprise: a first subset of interface elements each configured to engage a drive assembly interface and instrument interface to thereby transfer mechanical drive through the drape to actuate a first joint of the instrument; and a second subset of interface elements each configured to engage a drive assembly interface and instrument interface to thereby transfer mechanical drive through the drape to actuate a second joint of the instrument.

The plurality of interface elements may comprise a third subset of interface elements each configured to engage a drive assembly interface and instrument interface to thereby transfer mechanical drive through the drape to actuate a third joint of the instrument.

The drape may comprise a first, second and third pocket each formed from the covering, each pocket configured to receive a respective lug protruding from a proximal portion of the instrument, the drape being configured so that the first subset of interface elements are attached to the first pocket, the second subset of interface elements are attached to the second pocket, and the third subset of interface elements are attached to the third pocket.

The first subset of interface elements may be configured to engage respective instrument interfaces located on a first lug, the second subset of interface elements are configured to engage respective instrument interfaces located on a second lug and the third subset of interface elements are configured to engage respective instrument interfaces located on a third lug.

The drape may comprise a pocket formed from the covering and configured to receive a lug protruding from a proximal portion of the instrument, the pocket having at least one interface element attached thereto configured to engage a drive assembly interface and an instrument interface located on the lug to thereby transfer mechanical drive through the drape to actuate a first joint of the instrument.

The drape may comprise a first, second and third pocket each formed from the covering, each pocket configured to receive a respective lug protruding from a proximal portion of the instrument, each pocket having at least one interface element attached thereto configured to engage a drive assembly interface and an instrument interface located on the respective lug to thereby transfer mechanical drive through the drape to actuate a respective joint of the instrument.

According to a second aspect of the present disclosure there is provided a surgical robotic system for performing robotic surgery, the robotic system comprising: a surgical robot comprising an instrument having at least one joint, and a robotic arm comprising a drive assembly configured to provide mechanical drive for selectively actuating the at least one joint, the instrument and drive assembly each having a plurality of interfaces for coupling mechanical drive from the drive assembly to the instrument; and a surgical robotic drape comprising: a covering that envelopes the surgical robot drive assembly to define a sterile boundary thereover; and a plurality of interface elements that each engage with both a drive assembly interface and instrument interface to couple the drive assembly to the instrument to thereby transfer mechanical drive provided by the drive assembly through the drape to selectively actuate the at least one joint of the instrument, the plurality of interface elements being attached to the covering in a spatial arrangement so that each of the plurality of interface elements is separated from each of the other plurality of interface elements by material of the covering.

BRIEF DESCRIPTION OF FIGURES

The present invention will now be described by way of example with reference to the accompanying drawings. In the drawings.

DETAILED DESCRIPTION

Figure 1:
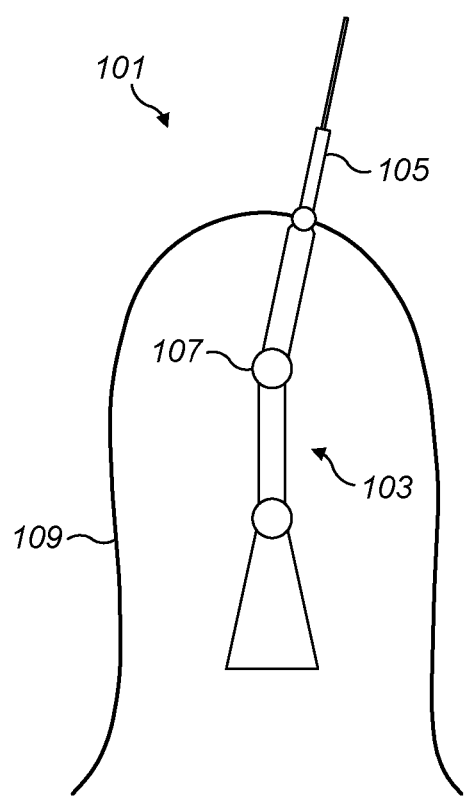
FIG. 1 shows a surgical robot set up to perform robotic surgery.
Figure 2:
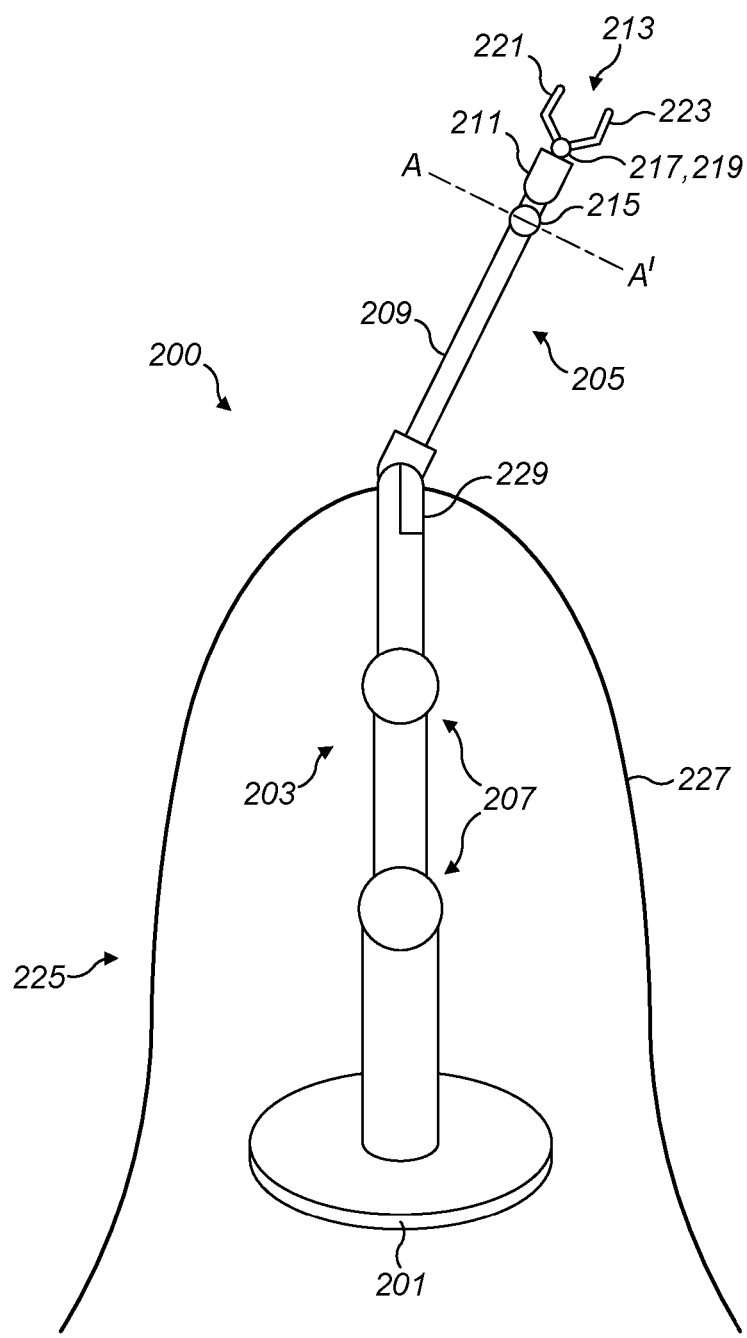
FIG. 2 shows a surgical robot set up to perform robotic surgery comprising an instrument with multiple motional degrees of freedom.

FIG. 2 shows an example of a surgical robot 200 for performing surgery. The robot comprises a base 201, a robotic arm 203 and a surgical instrument 205. The robotic arm is attached at its proximal end to the base. The instrument is releasably attached to the distal end of the robotic arm. The base may be used to secure the robot to a suitable anchor point during use. The base may be used to secure the robot to the floor of the operating theatre, or to the ceiling for example. The robotic arm may comprise a plurality of articulations, indicated generally at 207. The articulations permit the robotic arm to be moved to a range of positions and orientations under the control of an operator for performing a surgical procedure.

A surgical drape 225 comprises a covering 227 that envelopes, or shrouds, the robotic arm to define a sterile boundary thereover. The covering may be flexible so as to permit a degree of compliance to make it suitable for use with a range of robotic arms of differing sizes and shapes. The covering may be made of material such as polyester, polypropylene, polyethylene or polytetrafluoroethylene (PTFE) for example. The surgical drape is used to define a sterile environment during robotic surgery. The environment exterior of the drape (including the instrument 205) is preferably sterile during a surgical procedure. It is often difficult and impractical to sterilise the robotic arm due to its size and because it contains components such as motors and drive assemblies that cannot withstand sterilisation. The drape is therefore used to envelop the robotic arm and maintain the sterile surgical environment.

The instrument may be releasably connected to the robotic arm. This permits the instrument to be removed from the arm so that the instrument may sterilised or replaced in the period between surgical procedures. It also permits personnel such as technicians and surgeons to replace the instrument during a procedure. The instrument connects to the robotic arm through the drape 225 (as will be described in more detail below) so that the sterile boundary can be maintained.

The instrument 205 comprises a shaft 209, attached at its proximal end to the robotic arm, and a wrist member 211 attached to the distal end of the shaft. The wrist is attached at its other end to an end effector 213. The wrist is attached to the shaft by joint 215 which permits the wrist to pivot with respect to the shaft about an axis A-A' generally transverse to the elongate extent of the shaft (a "pitch joint"). The instrument may be configured so that the wrist can additionally pivot about a second axis transverse to both the axis of joint 215 and the elongate extent of the shaft, and rotate about a third axis that lies along the longitudinal extent of the shaft. The wrist may thus have three degrees of freedom. The end effector comprises a pair of grippers 221 and 223 attached to the wrist by respective joints 217 and 219, thus enabling each jaw to be independently pivoted with respect to the wrist about axes generally transverse to the longitudinal extent of the wrist.

It will be appreciated that the articulations shown here are examples and that the surgical instrument may comprise any number of joints. The one or more joints may comprise pitch joints, roll joints (rotation about an axis generally along the extent of the instrument), or a combination thereof. Further, the end effector need not comprise a pair of grippers, but may instead comprise a surgical tool such as a blade or cauteriser.

The robotic arm comprises a drive assembly 229 for selectively actuating the joints of the instrument (e.g. to pivot the wrist member 211 and/or the grippers of the end effector). The drive assembly may be configured to mechanically drive these joints. The drive assembly may be housed within the robotic arm. This is desirable because it reduces the cost and size of the instrument, which may be particularly important if the instruments are disposable. The drive assembly may be powered by one or more motors or servomechanisms that produce linear and/or rotary motion. The drive assembly may be capable of actuating each of the instrument joints separately and independently of each other. That is, the drive assembly can selectively actuate the joints. The drive assembly may be capable of actuating a plurality of joints simultaneously.

Figure 3:
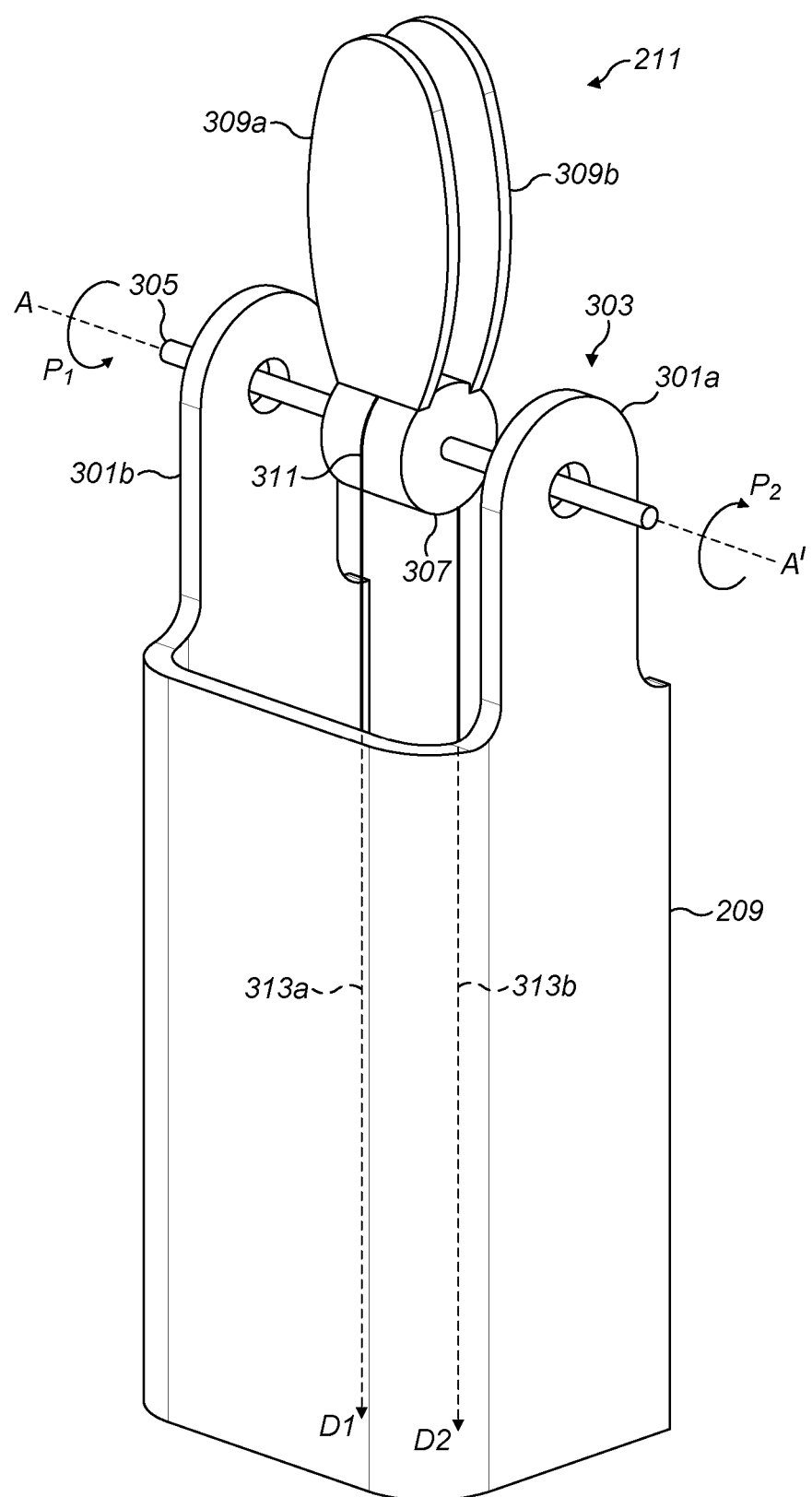
FIG. 3 shows two segments of a surgical instrument connected together by a joint.

FIG. 3 illustrates one way in which the instrument joints may be driven by the drive assembly of the robotic arm. FIG. 3 shows the articulation between the wrist member 211 and instrument shaft 209. The distal end of the shaft 209 comprises two opposing arms $301_a$ and $301_b$ which together the main body of the shaft form a clevis 303. A rod or axle 305 extends laterally across the shaft in a direction generally transverse to the longitudinal extent thereof and passes through both arms $301_{a,b}$. The rod defines the axis of joint 215, which is denoted by the dashed line A-A'. Mounted onto the rod is a pulley 307. The pulley may be fixedly mounted, or integral with the rod so that the rod and pulley rotate together about the axis A-A'. In this case the rod may be mounted to the clevis on bearings to permit rotation of the rod relative to the clevis. Alternatively the pulley may be mounted on the rod to permit relative rotation between the pulley and rod, with the rod fixedly secured to the clevis. Rigidly secured to the pulley is a pair of second opposing arms $309_{a,b}$, which form part of the wrist member 211. The remaining parts of the wrist member and the end effector have been omitted from this figure for clarity. The wrist member may for example comprise a housing, or casing that can be secured to the opposing arms $309_{a,b}$.

A cable or drive belt 311 is draped or looped over the pulley 307. That is, the cable is in contact with the pulley and extends along a portion of its circumference. The cable may sit within a groove on the pulley to reduce lateral motion of the cable with respect to the pulley. Looping the cable over the pulley forms two cable segments, denoted $313_a$ and $313_b$, which each extend from opposing sides of the pulley towards the proximal end of the shaft.

To actuate joint 215 to cause the wrist to pivot relative to the instrument, segments $313_a$ and $313_b$ of the pulley undergo reciprocal motion. For example, if segment $313_a$ is pulled downwards towards the proximal end of the shaft (denoted by the arrow $D_1$), the wrist pivots about axis A-A' in the direction of the arrow $P_1$. Alternatively, if segment $313_b$ is pulled downwards to the proximal end of the shaft (denoted by the arrow $D_2$), the wrist pivots about axis A-A' in the direction of the arrow $P_2$, opposite to the direction $P_1$.

Although in FIG. 3 only the wrist joint 215 is shown it will be appreciated that the other joints of the instrument may be driven in an analogous way (e.g. joints 217 and 219). Each instrument joint may be driven by its own pulley. Each pulley may have its own cable. An instrument may therefore have a separate cable for actuating each joint.

For example, an instrument with a wrist joint and two separately controllable end effectors may comprise three pulleys and three cables.

It will be appreciated that instead of a single cable 311 looped over the pulley, two separate cables each secured to opposing sides of the pulley can be used. In this case the two cable segments $313_{a,b}$ would correspond to two different cables. Thus in this arrangement each joint may be driven by a pulley and a pair of cables, and thus the instrument may comprise a pair of drive cables for each joint.

Figure 4:
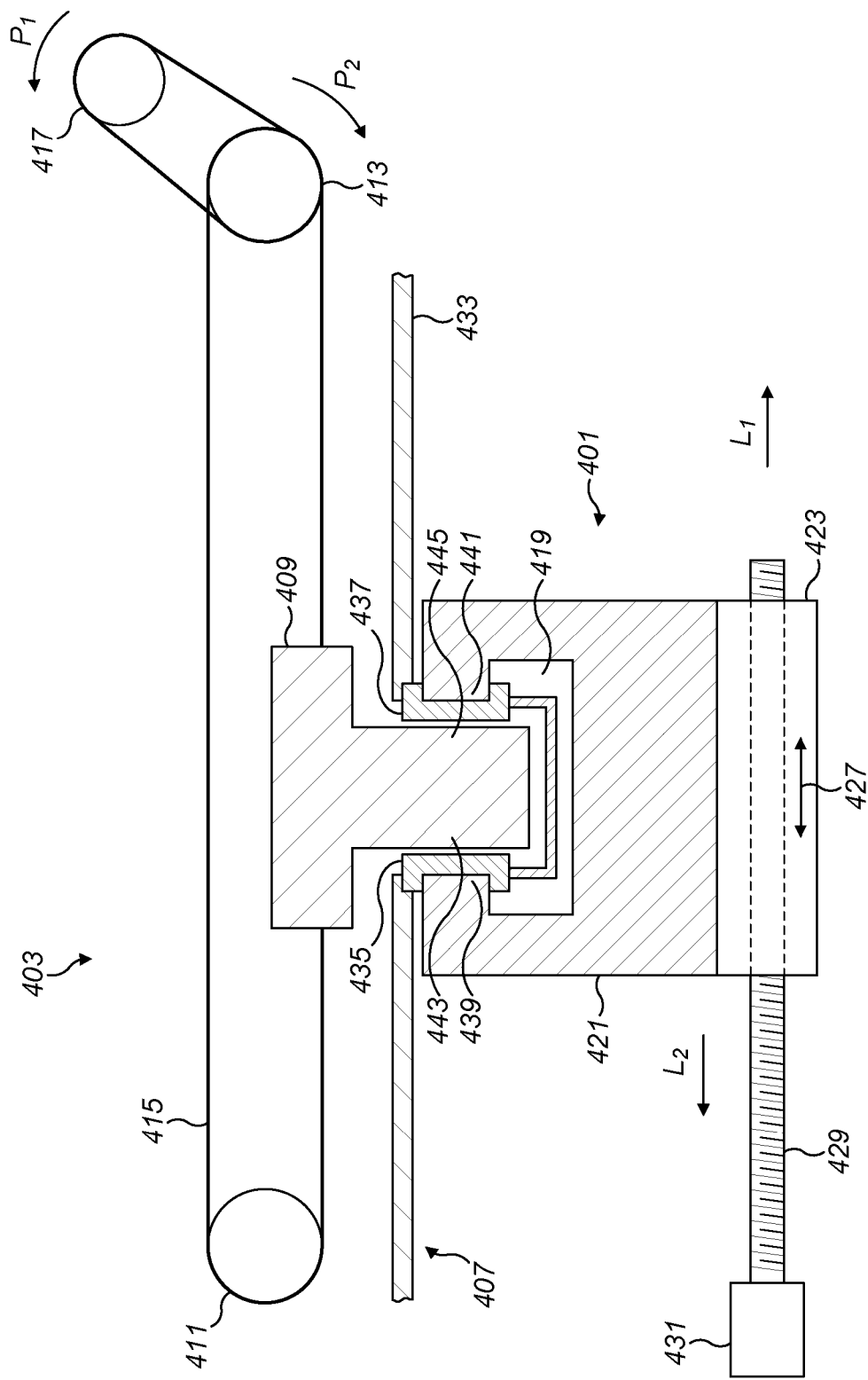
FIG. 4 shows a side view of a robotic arm drive assembly coupled to a surgical instrument through a surgical drape so that motion of the drive assembly can be transferred through the drape to actuate an instrument joint.

The drive assembly operates to actuate selected joints of the instrument by causing the appropriate cables within the instrument to undergo reciprocal motion. The drive assembly may be configured to actuate a selected joint or a selected plurality of joints by driving the appropriate pulleys within the instrument. Because the drive assembly and the surgical instrument are separated by the surgical drape 225, the mechanical drive produced by the drive assembly needs to be coupled, or connected to the instrument through the drape. FIG. 4 is an example of one way that the drive assembly can be coupled to the instrument through the drape.

Shown in FIG. 4 is a drive assembly, indicated generally at 401, and a surgical instrument indicated generally at 403, both shown in cross-section as indicated by the dashed markings. The housing, or outer casing, of the instrument has been omitted in this figure for clarity. The drive assembly 401 is housed within a robotic arm (not shown), such as robotic arm 203 shown in FIG. 2.

The surgical instrument and drive assembly are separated by a surgical drape 407 that envelopes the drive assembly to define a sterile boundary thereover. The instrument comprises a lug 409, and pulleys 411 and 413 driven by a drive cable 415. Cable 415 is fixedly attached to the lug so that movement of the lug causes a corresponding movement of the cable. The lug may be located at the proximal end of the instrument to enable the instrument to be connected to the robotic arm. Pulleys 411 and 413 may be housed within the shaft of the instrument, for example. The instrument further comprises pulley 417. Pulley 417 may be housed within a different segment of the instrument, for example within the wrist. Pulley 411 may be located at the proximal end of the instrument shaft and pulley 413 at the distal end to define an instrument joint. Pulley 413 may correspond to pulley 307 shown in FIG. 3, for example. Thus pulley 413 may define the wrist joint of the instrument. The instrument may further comprise an end effector (not shown) attached to the distal end of the wrist.

The instrument may further comprise additional pulleys and cables for actuating further instrument joints. Only a single joint is shown in this figure for the purposes of illustration. The instrument may also additionally comprise gear reductions etc.

The drive assembly comprises a socket 419 configured to receive the instrument lug. The socket forms part of a carriage 421. The carriage is secured to a support base 423 which comprises a bore 425 extending therethrough. The drive assembly further comprises a linear actuator to linearly displace the carriage bi-directionally as indicated by the arrows 427. In this example the linear actuator comprises a leadscrew 429 powered by a motor 431. The thread on the lead screw mates with a corresponding thread in the bore so that rotation of the lead screw causes linear motion of the support base, and thus carriage. The support base thus functions as a lead screw nut. Rotation of the lead screw can be controlled by the motor 431.

The drape 407 comprises a covering 433 and a plurality of interface elements 435 and 437. In this example the drape comprises two interface elements. The interface elements are fixed to the covering in a spatial arrangement so that each interface element is spatially separated from the other by the material of the covering. That is, each of the interface elements is retained, or secured, in place by the material of the covering, rather than the plurality of elements being retained by a common plastic plate.

The interface elements of the drape are configured to engage with both a drive-assembly interface and an instrument interface. Each interface element may comprise a first interfacing surface to engage a drive-assembly interface, and a second interface element to engage an instrument interface. The first and second interfacing surfaces may be opposing surfaces. They may be on opposing sides of the covering. The drive-assembly interface is the part of the drive assembly that faces the interface element when the drape is secured to the drive assembly. In this example the drive assembly interfaces are the interior facing surfaces of the socket 439 and 441. The instrument interface is similarly the part of the instrument that faces the interfacing elements when the instrument is coupled to the drive assembly through the drape. In this example the instrument interfaces are the two sub-sections of the lug 443 and 445.

The drive assembly interfaces and/or instrument interfaces may alternatively be specific components (e.g. studs) that engage the interface elements. The first interfacing surface may be configured to engage a complementary surface of the drive assembly interface and the second interfacing surface may be configured to engage a complementary surface of the instrument interface. This may facilitate a secure engagement. In this example the instrument interfaces do not have complimentary surfaces but are instead the two portions of the outer surface of the lug that face the interface elements 435 and 437. Various examples of interface elements will be described in more detail below.

By engaging the interfaces of both the drive assembly and the instrument, the interface elements enable the drive assembly to be coupled to the instrument through the drape. This enables mechanical drive provided by the drive assembly to be transferred through the drape to the instrument to actuate one or more of the instrument's joints. For example, the plurality of interface elements can transfer linear mechanical drive provided by the drive assembly linearly through the material of the drape to selectively actuate a joint of the instrument. For example, rotation of lead screw 429 may cause the carriage to move in the linear direction denoted by the arrow $L_1$. This linear motion is transferred from the carriage 421 to the instrument interface 409 via the interface elements of the drape, thus causing corresponding motion of the lug. This motion of the lug drives the instrument cable 415 and pulleys 411 and 413 in an anti-clockwise direction. Driving pulley 413 in this direction drives the instrument joint and causes the wrist to pivot relative to the shaft in a direction $P_1$. Similarly, rotating the lead screw to drive the carriage in the direction $L_2$ causes the wrist to pivot in the direction $P_2$.

The interface elements act as reinforcement elements, or structures to the covering. This is advantageous because motion of the drive assembly subjects the drape to potentially large displacements and shear forces that would otherwise damage the material of the covering. However, because the assembly is coupled to the instrument through the interface elements, the drive forces are transmitted through the interface elements thus preventing damage to the covering. Preventing damage or rupture to the covering may be particularly important because it helps to maintain the sterile barrier during a surgical procedure.

The material of the covering may suitably be flexible, or deformable. The covering may have a degree of elasticity. The material could be polythene, for example. Because each interface element of the drape is spatially separated from each of the others by the material of the covering, permitting an amount of flexibility, or compliance, or deformability of the covering permits the relative spatial arrangement of the elements to be adjusted. That is, each interface element is not spatially fixed with respect to each of the other interface elements. The spatial arrangement of the interface elements may as such be dependent upon the configuration or arrangement of the covering.

For example, if the covering was stretched, folded or twisted whilst securing the drape to the drive assembly interface, the interface elements may move spatially relative to each other thereby altering their spatial arrangement. As a further example, the interface elements may have a first spatial arrangement when the drape is in a planar configuration and a second, different spatial arrangement when the drape is folded, or the planar arrangement deformed in some way. This is advantageous because it may permit the drape to be fitted to a variety of different robotic arms and instruments. For example, each type of surgical robotic arm may have a different drive assembly, and as such the layout or configuration of the drive-assembly and instrument interfaces may vary. However because the spatial arrangement of the drape interface elements is variable, the drape may be manipulated to cover a range of different drive assemblies. This may not be possible for prior art systems in which the interface elements are retained in a rigid plastic plate.

In alternative examples, the instrument may comprise a plurality of lugs located at its proximal end. The instrument may for example comprise three lugs. Each lug may be mechanically coupled to a respective instrument joint. The lugs can be selectively driven by the drive assembly to thereby selectively actuate the instrument joints. The drape may comprise interface elements configured to engage instrument interfaces located on each of these lugs.

An example of how the drape may be secured to the robotic arm will now be described. When the surgical robot is to be prepared for a procedure, the instrument is detached from the robotic arm. The drape 407 is then placed over the robotic arm to cover the arm, including the drive assembly. The drape is fitted into place on the robotic arm by engaging the interface elements of the drape with the drive-assembly interface. The interface elements may for example be snap-fitted, push-fitted or slotted into place so that the interface elements are secured to the drive assembly interface. Once the drape is fitted in place over the arm, the instrument is coupled to the drive assembly to secure the instrument relative to the robotic arm. The instrument is fitted into place by engaging the interface element of the drape with the instrument interface. In this example this involves placing the instrument lug into the socket of the drive assembly. The interface elements may be configured to securely engage the instrument interface. Thus in addition to transferring drive to the instrument, the interface elements can additionally operate to secure the drape to the robotic arm. This is advantageous because it enables the drape to be secured to the arm without requiring a separate plate in the drape to perform this function, thus reducing the number of components of the drape. For example, each interface element may comprise a projection that can be received by respective slots located on the instrument interface.

The interface elements may suitably be configured to releasably engage the instrument and drive assembly interfaces so that the drape can be detached from both the instrument and the robotic arm. The interface elements may be configured so that they can be detached from the drive assembly interface and instrument interface separately and independently of each other. For example, it may be desirable to replace the instrument during a surgical procedure. In this case the instrument can be detached from the drape whilst still leaving the drape attached to the robotic arm. At the end of the procedure, the drape can also be detached from the robotic arm so that it can be discarded or re-sterilised. Features of the interface element that enable engagement with the instrument and drive assembly interfaces will be discussed in more detail below.

Figure 5:
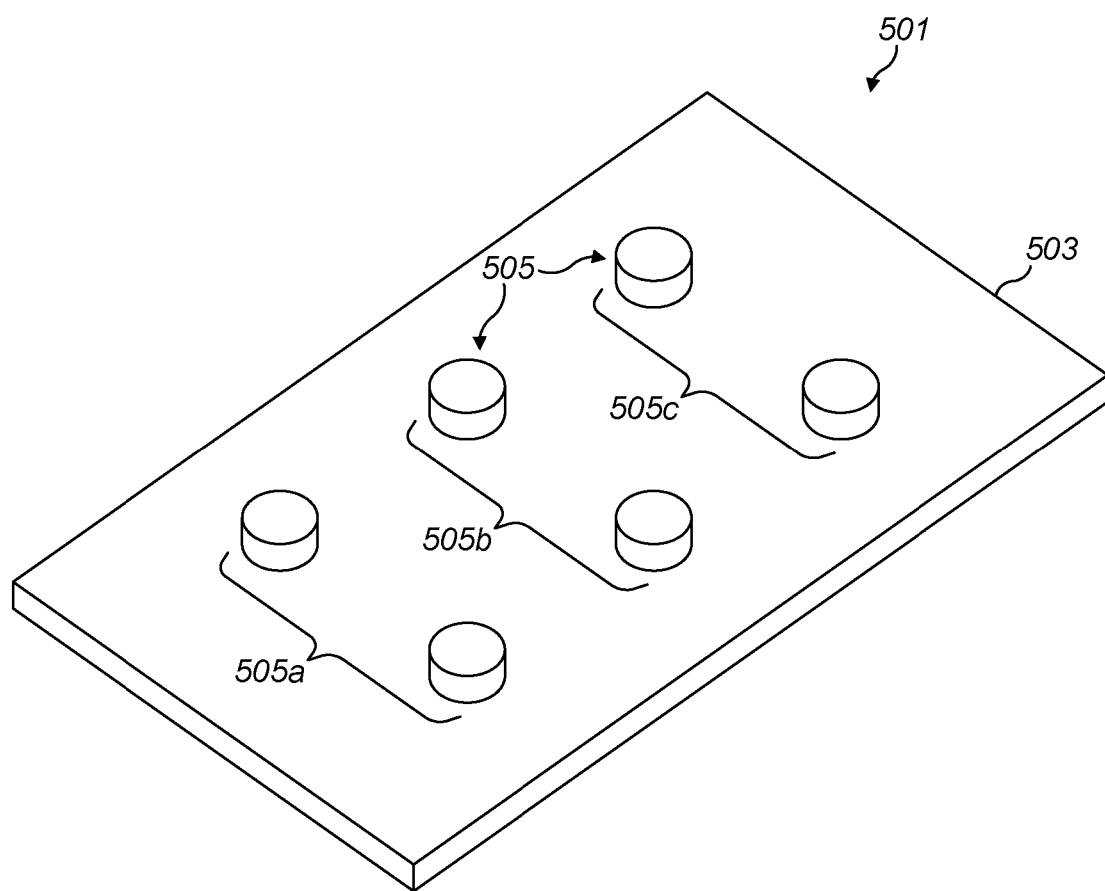
FIG. 5 shows an example of a surgical drape in a planar configuration that comprises a plurality of interfacing elements for coupling the robotic arm to the instrument through the drape.

FIG. 5 shows an example of a surgical drape 501 in a planar arrangement. The drape comprises a covering 503 and a plurality of interface elements 505. Each interface element is configured to engage both a drive assembly interface and an instrument interface to transfer mechanical drive provided by the drive assembly through the drape to the instrument to actuate at least one joint of the instrument.

The interface elements are fixed to the covering in a spatial arrangement so that each interface element is spatially separated from each of the other interface elements by the material of the covering. As described above, the covering may be flexible, or deformable, or pliable so that the interface elements are not spatially fixed with respect to each other. The interface elements shown are for engaging one or more drive-assembly interfaces of a single robotic arm that couples to a single instrument. That is, the interface elements that are spatially separated by material of the covering are configured to engage drive-assembly and instrument interfaces to couple the drive assembly of one robotic arm to one instrument to thereby transfer motion from the drive assembly to actuate one or more joints of that instrument. The reference to 'one instrument' does not mean that the drape is incapable of being used with a range of different instruments, but rather that the set of interface elements are used in a one-to-one coupling between robotic arm and instrument (as opposed to the set of interface elements being used to couple multiple robotic arms to multiple instruments simultaneously). The drape may however be configured to comprise multiple sets of interface elements, each set being used to couple a robotic arm to an instrument. Such a drape may be suitable for use with surgical robots that comprise multiple robotic arms.

Drape 501 may be suitable for coupling motion between a drive assembly and an instrument that comprises three joints. For example, the plurality of interface elements may be viewed as comprising three subsets of elements (denoted $505_{a,b,c}$). Each subset can be configured to engage drive-assembly and instrument interfaces to couple the drive assembly to the instrument to thereby transfer motion of the drive assembly to actuate a respective joint of the instrument. In this case, subset $505_a$ can be used to transfer motion to actuate a first instrument joint; subset $505_b$ can be used to transfer motion to actuate a second instrument joint; and subset $505_c$ can be used to transfer motion to actuate a third instrument joint. Referring to FIG. 4, each subset of interface elements may be configured to engage with a respective instrument lug, for example. Of course, this is just an example and the drape may comprise any suitable number of interface elements for transferring motion from a drive assembly to an instrument to actuate any suitable number of joints.

The interface elements may be adhered, fixed, attached or mounted to the covering during manufacture of the drape. They may for example be bonded, thermoformed or clipped to the material covering. They may be pushed into or clipped onto the covering before the covering is thermoset.

The interface elements may be in the form of studs. The studs may take various forms, for example they may be discs, buttons or plates. They may be made of metal, or a suitably hard plastic such as PVC, polypropylene, acrylic etc. Various examples of interface elements are shown in FIG. 6

Figure 6:
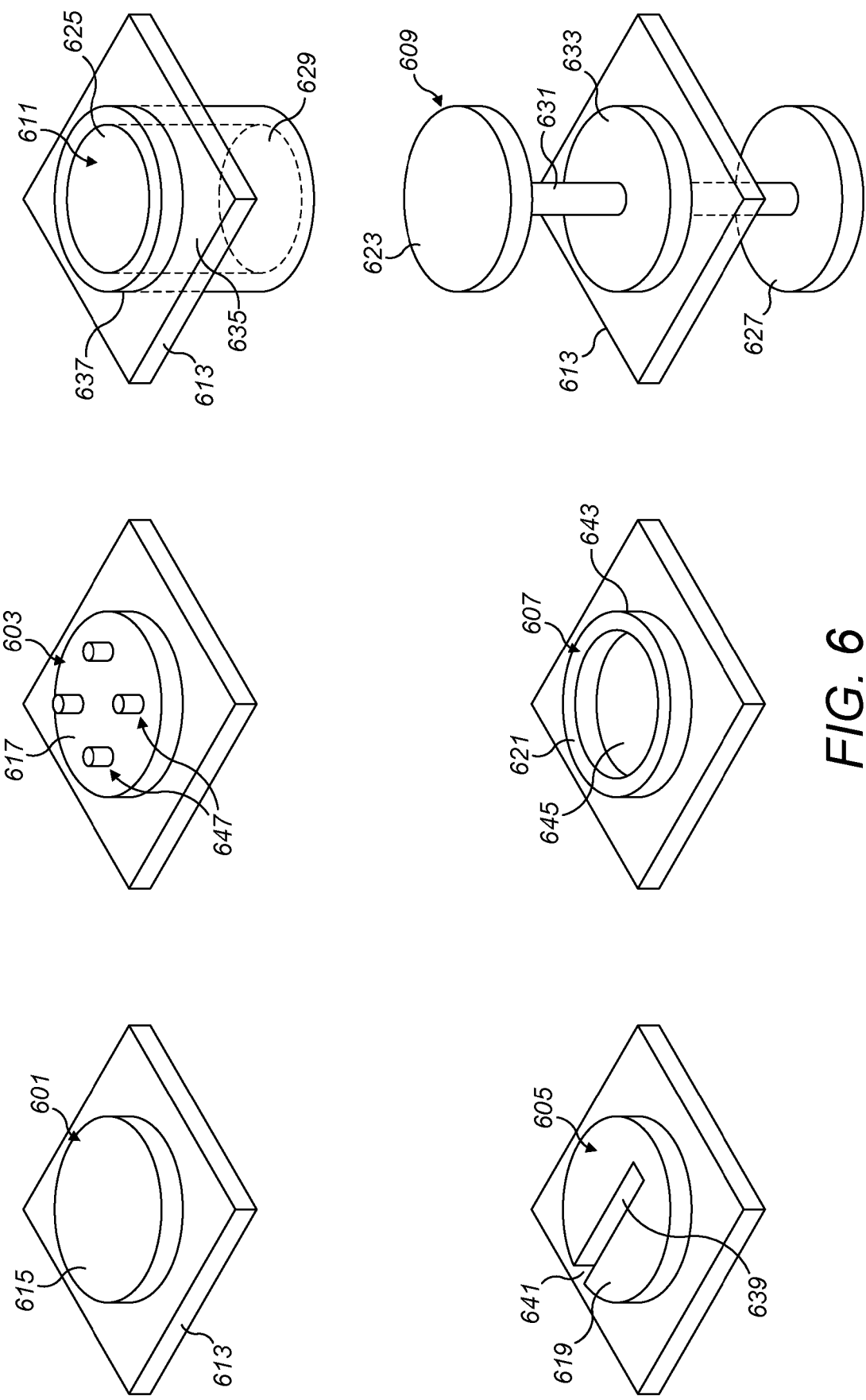
FIG. 6 shows several examples of interfacing elements.

Shown in FIG. 6 are a range of interface elements 601, 603, 605, 607, 609 and 611. Each interface element is shown retained by a region of surrounding covering material 613. Each interface element comprises a first interfacing surface (denoted 615, 617, 619, 621, 623 and 625 respectively), and a second interfacing surface (shown only for elements 609 and 611 and denoted by 627 and 629 respectively). The first interfacing surface is for engaging one of a drive-assembly interface and instrument interface, and the second interfacing surface is for engaging the other one of the drive-assembly and instrument interface.

The interface elements may be configured to engage the interfaces of the drive assembly and instrument to transfer linear motion through the drape, for example as shown in FIG. 4. The interface elements may as such be securely retained in place by the material of the covering. That is, the elements may be fixedly secured or mounted to the covering material, e.g. using one of the methods described above. An example of such an interfacing element is shown at 601. Element 601 may be in the form of a simple plastic stud, or disc. This interface element has the advantage of being relatively simple and cheap to manufacture.

The interface elements may alternatively be configured to engage the interfaces of the drive assembly and instrument to transfer rotary motion through the drape. In this case the drive-assembly and instrument interfaces may be in the form of rotating elements such as spools, or capstans. The drive-assembly interface may be driven by a rotary actuator, such as a motor. The instrument spool may be attached to a drive cable configured to drive a pulley (such as pulley 413 or 307). Rotation of the instrument spool causes the pulley to rotate via action of the drive cable, thus actuating a joint in the instrument. The interface elements may be configured so that the first and second interfacing surfaces are configured to rotate relative to the surrounding covering material 613. The elements may be configured so that rotation of one of the interfacing surfaces causes a corresponding rotation in the other of the interfacing surfaces.

In operation, the drive assembly may cause one or more of the drive-assembly interfaces to rotate. This rotation causes the interfacing surfaces of each engaged element to also rotate. The rotation of the interfacing surfaces is transferred to the engaged instrument interfaces thereby causing them to also rotate. Thus rotary motion of the drive assembly can be transferred through the drape to the instrument.

Examples of rotating interface elements are shown generally at 609 and 611. Interface element 609 comprises first and second interfacing surfaces 623 and 627. Each surface is mounted on an axle 631 that extends through a mounting plate 633. The axle is configured to be rotatably secured to the mounting plate to permit relative rotation therebetween. The mounting plate is fixed to, or retained by the material of the covering 613. Thus rotation of one of the interfacing surfaces cause a corresponding rotation in the other of the interfacing surfaces.

An alternative example of a rotating interface element is shown at 611. The interface element comprises first and second interfacing surfaces 625 and 629 that form part of a drum 635. The drum is rotatably mounted within an outer casing, or frame 637. The casing is fixed to, or retained by the material of the covering 613

An interface element may suitably be configured to transfer both linear and rotary motion from the driving assembly to the instrument. Thus the interface element may be configured so that its first and second interfacing surfaces can rotate relative to the surrounding covering material to transfer rotational drive to the instrument when engaged with the drive assembly and instrument interfaces, and also use that engagement to transfer linear drive from the drive assembly. The interface element may transfer rotational drive to actuate a first instrument joint and transfer linear drive to actuate a second instrument joint. Thus an interface element may be capable of transferring motion to actuate two joints.

In this case, the driving assembly may comprise both a linear actuator and a rotary actuator. The linear actuator may cause linear motion to be transferred through the interface element, for example as described with reference to FIG. 4. This linear motion drives a cable within the instrument to in turn drive a pulley to actuate one of the instrument joints. The rotary actuator may cause the interfacing surfaces of the interface element to rotate. This causes a corresponding rotation in the instrument interface that drives a second cable to in turn actuate a second instrument joint. Thus the instrument interface is configured to undergo both linear movement and rotary movement. The linear motion drives a first cable and pulley in the instrument (and thus actuates a first joint), and the rotary motion drives a second cable and pulley in the instrument (and thus actuates a second joint). The instrument interface could take the form of a spool or capstan rotatably mounted to a lug capable of undergoing linear motion. The drive-assembly interface could take the form of a spool or capstan rotatably mounted to a carriage driven by a linear actuator.

Configuring the interface elements to transfer both linear and rotary motion is advantageous because it may reduce the number of interface elements required to be fixed to the drape covering. This is because multiple cables (and thus multiple instrument joints) may be driven through a single interface element.

The interfacing surfaces of the interface elements may comprise surface features that assist the interface element in engaging the drive-assembly and instrument interfaces. The surface features may be configured to interface, mate or connect with complementary surface features on the drive-assembly and instrument interfaces. The surface features may be configured to hold the interface element fast with the instrument and drive-assembly interfaces. The surface features may nevertheless enable the interfacing element to be disengaged from both the drive-assembly and instrument interfaces in response to a suitable manual force. The manual force may be such as to prevent dislodgment of the interface element in response to minor forces caused by accidental knocks etc. (so that the drape and/or instrument are not accidentally removed during surgery), but not so strong as to prevent the drape from being detached from the robotic arm and/or instrument manually.

The surface features of interfacing element may mate with the complementary features on the drive-assembly and instrument interfaces to form a push-fitting, or snap-fitting. An example of such a surface feature is shown at 603.

The first interfacing surface 617 of element 603 comprises a plurality of projections 647 extending generally transversely to the plane of the interfacing surface. The projections are configured to mate with corresponding grooves, or recesses in the drive-assembly and instrument interfaces. The projections may be push-fitted or snap-fitted into place. In this example the projections are shown in the form of lugs, however it will be appreciated the projections may take other forms, for example ridges. Alternatively, the interfacing surface may comprise grooves or recesses configured to mate with corresponding projections on the drive-assembly and instrument interfaces. The interface element may comprise projections on one interfacing surface and recesses/grooves on the other interfacing surface.

Interface element 605 comprises a surface feature in the form of a guide slot 639. The guide slot is configured to receive a pin, or lug through an opening 641 located at one end of the slot. The pin may be shaped such that once in the slot the pin is prevented from moving in a direction transverse to the slot. Thus the pin can only enter or leave the guide slot through the opening. The pin/lug may be attached to the drive assembly and instrument interfaces. Thus to attach the interface element to the drive-assembly interface, a user can slide the slot on one interfacing surface 619 of the element over the pin on the drive assembly. The pin on the instrument interface can be slid into the guide slot on the opposing interfacing surface of the interface element. The slots and pins can thus hold the interface element fast with the interfaces of the drive assembly and instrument. Each interfacing surface may alternatively comprise more than one guide slot for receiving more than one pin/lug. It will also be appreciated that the interfacing element may alternatively comprise the pin/lug and the slots may be located on the drive-assembly and instrument interfaces. The interface element may comprise a slot on one interfacing surface and a pin/lug on the other interfacing surface.

Rather than mechanically mating the interface element to the drive-assembly and instrument interface (e.g. using surface features), the interface element may instead engage these interfaces using a magnetic connection. In the case of a magnetic connection, the interfacing surfaces of the interfacing element may be made or comprise a magnetic material. The instrument and/or drive-assembly interfaces may also be magnetic, or electromagnetic, with an opposing polarity to that of the interface element. Alternatively, only one of the interfacing surfaces may comprise a magnetic material. That is, the interface element may be configured so that one of its interfacing surfaces engages one of the instrument or drive assembly interfaces via magnetic connection, and the other one of its interfacing surfaces engages the other one of the instrument and drive assembly interface via mechanical connection.

The interface elements may be configured so that the interfacing surface that mates with the complementary surface of the drive-assembly interface, and the interfacing surface that mates with the complementary surface of the instrument interface are configured so that it requires a greater manual force to disengage the interface element from the drive-assembly than from the instrument. Thus the interface element may be attached, or engaged more firmly to the drive-assembly interface than the instrument interface. That is, the interfacing surfaces may be configured so that manually disengaging the instrument interface and interface element leaves the interface element engaged with the drive-assembly interface. This is advantageous because it enables a user (e.g. a nurse or technician) to detach the surgical instrument from the drape whilst leaving the drape attached to the robotic arm. Thus the instrument can be replaced during a surgical procedure whilst preserving the sterile boundary over the robotic arm.

One way for the interface element to be more securely attached to the drive assembly than the instrument is for the two interfacing surfaces of the interfacing element to have different surface features. That is, the surface that mates with the instrument interface may have different features from the surface that mates with the drive-assembly interface.

For example, if the surface features are in the form of projections (e.g. lugs and/or ridges), then the interfacing surface that mates with the drive-assembly interface may have a greater number of projections than the interfacing surface that mates with the instrument interface. This may mean that the interface element is more firmly attached to the driving assembly than to the instrument interface. Alternatively, if the interface elements engage the drive assembly and interface via a magnetic connection, the interface element may be configured so that the magnetic connection between the interfacing surface and the drive-assembly interface is greater, or stronger, than the magnetic connection between the interfacing surface and the instrument interface.

The interface elements may alternatively be in the form of an annulus, or ring. The ring could take a variety of shapes, for example it may be circular or ovular. It may be in the shape of a lozenge. An example of such an interface element is shown at 607. Interface element 607 comprises an annulus 643 that bounds, or circumscribes or defines an interior window 645. The annulus may be mounted to the material covering by push-fitting so that the annulus perforates the covering in the region interior of the annulus. Thus the window could be an opening that defines a passageway through the surface of the covering. The annulus can engage the drive assembly and instrument interfaces to couple the drive assembly to the instrument. The annulus may for example engage, or mate, with a complementary surface located on the drive assembly and instrument interface, such as a circular groove.

The opening 645 may be used to receive or channel a cable from the drive assembly through the drape to the instrument. The cable may for example be a power cable to power a tool attached to the distal end of the instrument shaft. The cable can extend from the robotic arm, through the opening to the instrument The opening 645 therefore allows a cable to be connected to the surgical instrument through the drape when the surgical robot is set up to perform a surgical procedure. This is advantageous because it permits an electrical connection between the robotic arm and instrument without requiring a cable to be placed along the exterior of the drape, where it would be in the sterile environment.

The annulus, or ring, may be configured to engage the drive-assembly and instrument interfaces so that one or both of these interfaces substantially seal, or close off the opening. Referring for example to FIG. 4, the instrument lug 409 may be substantially flush with the annuli of interface elements 435 and 437 so that the respective openings are substantially closed. The opening need not necessarily be fully closed however because the sterile boundary formed by the drape need not be hermetic.

In the examples described above, the surgical drape has been described as being formed in a planar configuration that is manipulable by a user to cover a robotic arm.

In an alternative example, the drape may be manufactured in a shape or configuration that makes it more suitable for attachment to an instrument and/or drive assembly. An example of such a drape is shown in FIG. 7.

Figure 7:
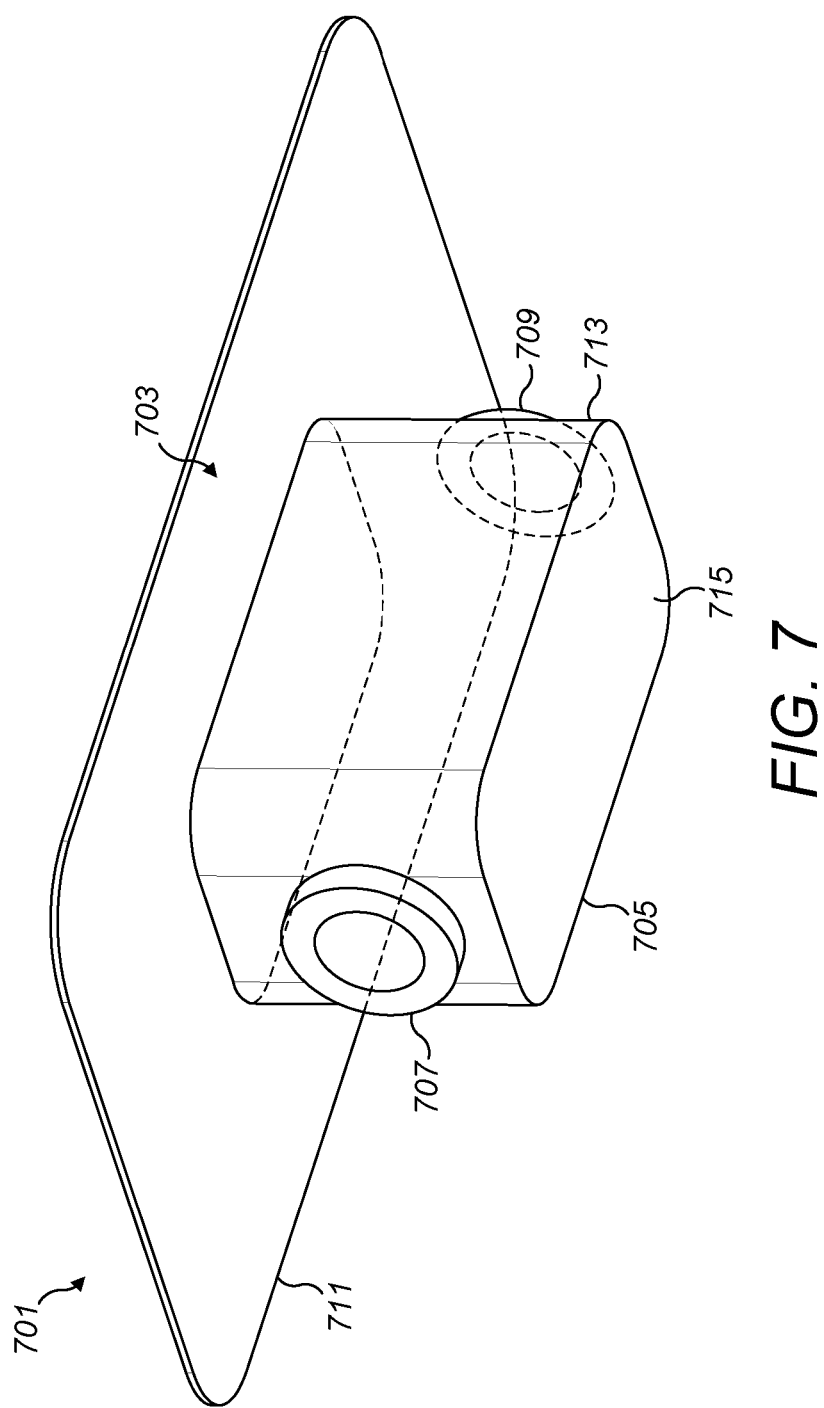
FIG. 7 shows an example of a surgical drape comprising a pocket for receiving a component of a robotic arm drive assembly or a surgical instrument.

FIG. 7 shows a drape 701 comprising a covering 703 for enveloping a robotic arm including the robotic arm drive assembly. Only a portion of the covering is shown for clarity. The drape further comprises a pocket 705 formed from the material of the covering. The covering material may be flexible, as described above. The covering may as such comprise a sheet, or planar portion 711 with the pocket being integral therewith. The pocket comprises side walls 713 extending in a direction generally transverse to the plane of the covering. The pocket further comprises a base 715 generally parallel to the planar portion of the covering and integral with the side walls.

In this example the pocket is a generally cuboidal shape though it will be appreciated that this is just an example and the shape of the pocket is entirely configurable by the manufacturer of the drape. The pocket may for example be square cuboidal, or cylindrical in shape.

Fixed to the pocket are interface elements 707 and 709, each configured to engage with both a drive-assembly interface and an instrument interface. The interface elements are spatially separated from each other by the material of the covering as described previously. In this example the interface elements are fixed to opposing sides of the pocket, and in particular to opposing sidewalls of the pocket. The interface elements may be of any of the types described herein. Each of the interface elements may be of the same type, or different types.

The pocket forms part of the covering. The pocket may be formed during manufacture of the drape, and may be formed before or after the interface elements have been attached. The pocket may for example be formed by thermoforming the drape/covering over a suitably shaped mould. The pocket may as such be a permanent feature of the drape. This is not to say that the covering is not flexible/deformable, but rather that the pocket is an inherent feature of the drape, as opposed to having been formed merely by manipulation of the covering by a user.

The pocket may be configured to receive, or house, a component of the instrument and/or drive assembly to enable their respective interfaces to engage the interface elements 707 and 709. The pocket may be configured to receive a portion of the surgical instrument and to mate or be received by a portion of the robotic arm drive assembly. Alternatively, the pocket may be configured to receive a portion of the drive assembly and to mate or be received by a portion of the instrument. For example, referring again back to FIG. 4, the pocket may be configured to receive the instrument lug 409 and to be received by the carriage 421 of the drive assembly. Thus the pocket sits within the carriage to enable the interface elements 707, 709 to engage the drive-assembly interfaces (and thereby attach the drape to the robotic arm). The instrument lug then fits within the pocket 705 to enable the interface elements to further engage the instrument interfaces to thereby couple the instrument to the drive assembly.

Forming a pocket within the covering may enable the interface elements to engage the respective interfaces of the drive assembly and instrument without requiring that the drape be substantially contorted or deformed. This may be beneficial in reducing the stress placed on the covering and thus reducing the chance that the drape damaged during use. It may also enable a user to more easily locate the interfaces of the drive assembly and instrument when setting the robotic arm up for a surgical procedure.

In this example the drape comprises two interface elements attached to the pocket. This is only for example and it will be appreciated that the drape may comprise any suitable number of interface elements. The drape may for example comprise a set of interface elements (e.g. two, three or more elements), with a first subset of those interface elements configured to engage respective drive-assembly and instrument interfaces to transfer motion of the drive assembly to actuate a first instrument joint, and a second subset of those elements configured to engage respective drive-assembly and instrument interfaces to transfer motion of the drive assembly to actuate a second instrument joint. In general, the drape may comprise a plurality of interface elements forming N subsets of elements for transferring motion of the drive assembly to drive a respective N instrument joints.

Figure 8:
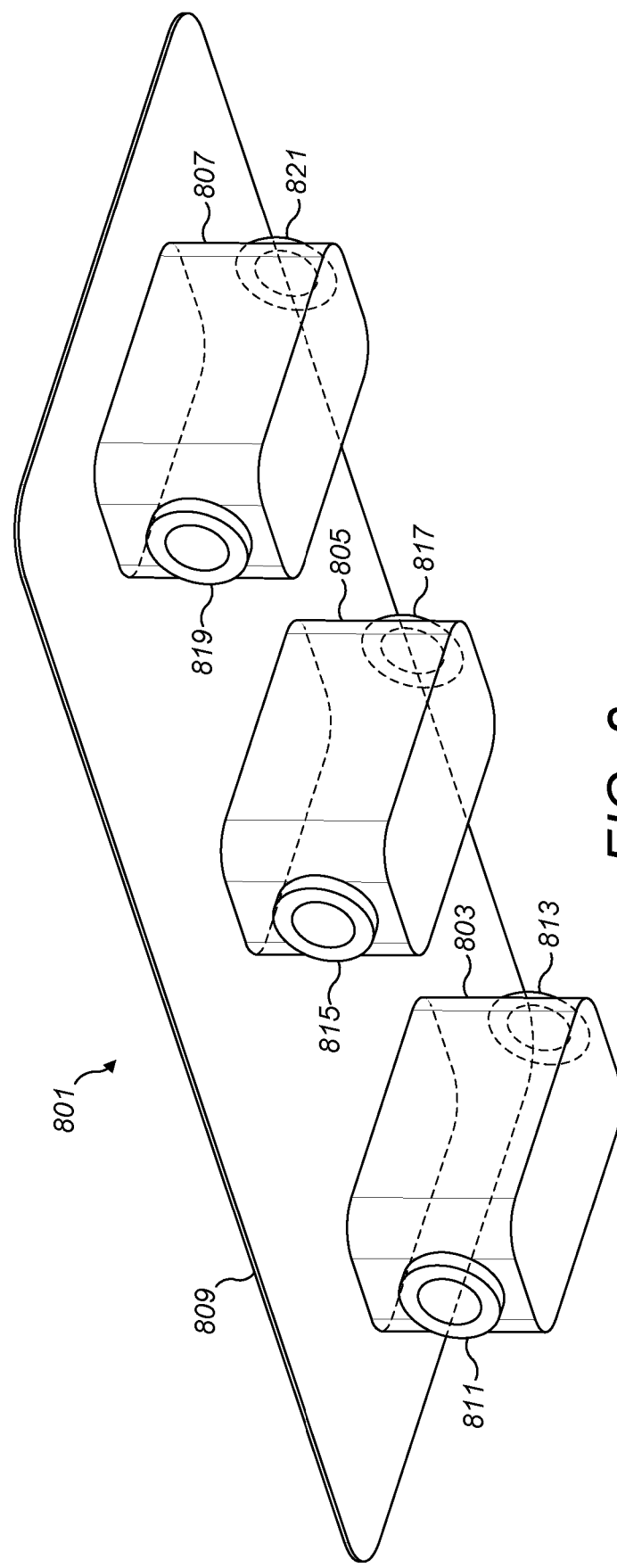
FIG. 8 shows an example of a surgical drape comprising a plurality of pockets.

In an alternative example, the drape may comprise a plurality of pockets formed from the covering. An example of such a drape is shown in FIG. 8. In this example, the drape 801 comprises three pockets 803, 805 and 807 formed from the covering 809. The drape comprises a plurality of interface elements 811, 813, 815, 817, 819 and 821. Interface elements 811 and 813 are attached to pocket 803; interface elements 815 and 817 are attached to pocket 805; and interface elements 819 and 821 are attached to pocket 807.

Each of the interface elements attached to the first pocket are for engaging respective interfaces of the drive assembly and instrument for transferring motion from the drive assembly to actuate a first instrument joint. Each of the interface elements attached to the second pocket are for engaging respective interfaces of the drive assembly and instrument for transferring motion from the drive assembly to actuate a second instrument joint. Similarly, each of the interface elements attached to the third pocket are for engaging respective interfaces of the drive assembly and instrument for transferring motion from the drive assembly to actuate a third instrument joint. Thus a first subset of the interface elements of the drape are attached to the first pocket for transferring mechanical drive to actuate a first joint, a second subset of the interface elements of the drape are attached to the second pocket for transferring mechanical drive to actuate a second joint, and a third subset of the interface elements of the drape are attached to the third pocket for transferring mechanical drive to actuate a third joint.

For example, the instrument may comprise three lugs, each of which is configured to be selectively driven in response to motion of the drive assembly to actuate a respective instrument joint. Each of the lugs may be of a similar form to what is shown in FIG. 4. The first pocket is configured to receive a first of these lugs, the second pocket is configured to receive a second of these lugs and the third pocket is configured to receive a third of these lugs. Although only three pockets are shown in FIG. 8, it will be appreciated that the drape may comprise any suitable number of pockets.

Described herein are various examples of a surgical drape comprising a plurality of interface elements. It will be appreciated that the plurality of interface elements on the surgical drape need not necessarily all be the same. That is, the interface elements may each be of the same type (e.g. one of the types discussed above), but they need not be. It will be appreciated that the type of each interface element fixed to the covering is entirely configurable. Thus, for example, the drape may comprise one or more interface elements that comprise surface features as in element 603 and/or 605, as well as one or more interface elements that are capable of rotation such as element 609 and/or 611. It may also be possible for an interface element to have differing first and second interfacing surfaces. Thus an interface element may have one interfacing surface that is magnetic, and one interfacing surface with a guide slot, for example.

The description above makes reference to instrument interfaces and drive-assembly interfaces. The instrument interface refers to the part of the instrument that faces the interface element when the interface element engages the instrument. It may be the surface or part of the instrument that is congruent with the interface element when the element engages the instrument. Similarly, the drive assembly interface refers to the part of the drive assembly that faces the interface element when the interface element engages the drive assembly. The instrument and/or drive assembly interfaces may comprise a complementary surface to the surface of the interface element with which they engage. Alternatively the instrument and/or drive assembly interfaces may have a surface that is not specifically designed to mate with the interface element. The instrument and/or drive assembly interfaces may be surfaces that are integral, or form part of, a larger surface. In this case the instrument and/or drive assembly interface refers to the subsection, or portion of that surface(s) that faces the interface element.

The drape may additionally comprise a guiding structure to assist a user in positioning the drape correctly with respect to the robotic arm so that the interface elements can engage the drive-assembly interfaces. The guiding structure may not engage either the drive-assembly or instrument interfaces. That is, the guiding structure does not act to provide drive from the drive assembly to the instrument but instead functions to more easily enable a user to position the drape so that the interfacing elements can engage the drive-assembly interfaces. This is advantageous for drapes for which the interface elements are retained by the drape material as opposed to a backing plate. For such drapes it may be difficult to easily position the drape due to the relatively small size of the interface elements compared to the overall size of the drape. Before describing how the guiding structure can connect to the robotic arm, an example of the distal end of the arm will first be described.

Figure 9:
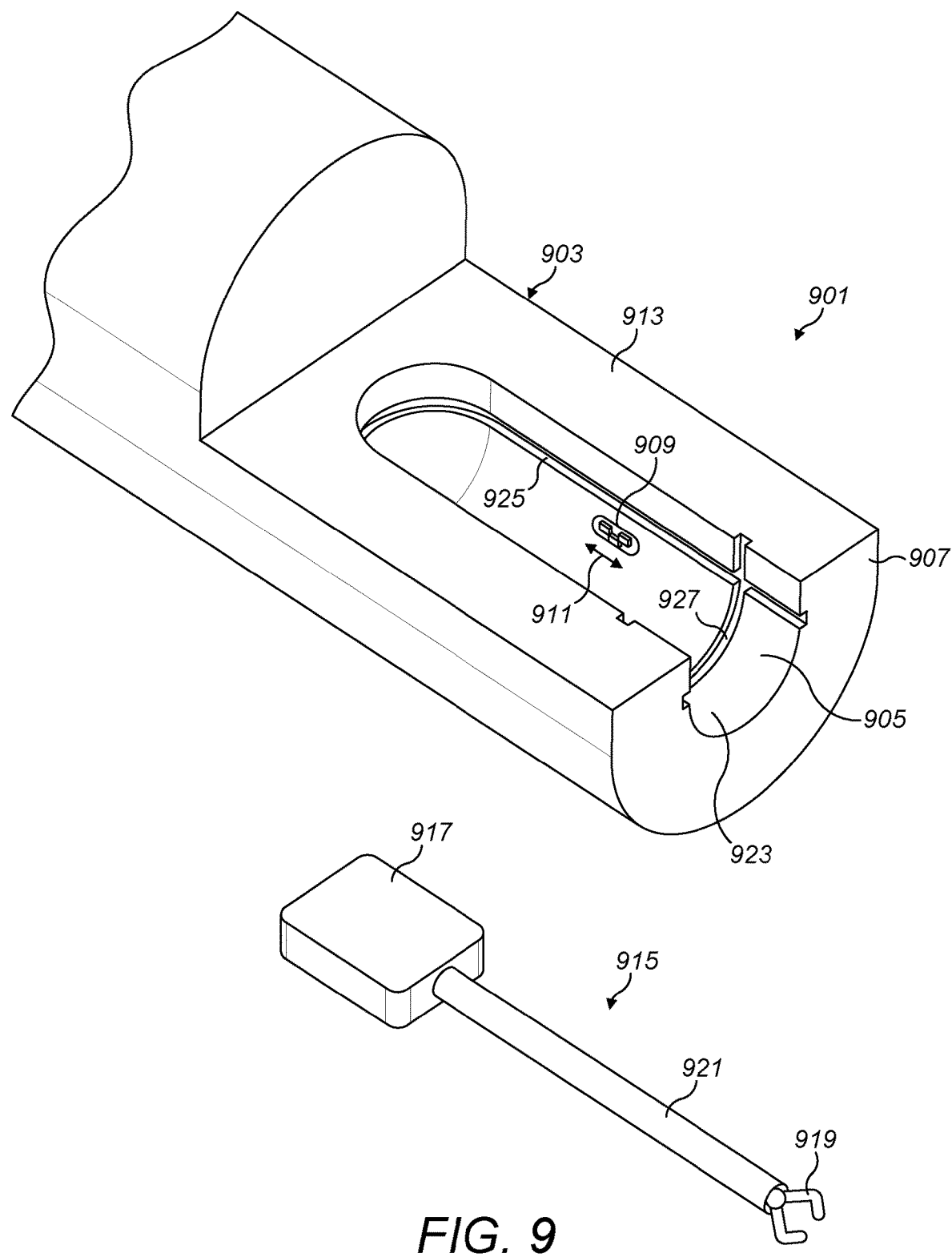
FIG. 9 shows a distal end of a robotic arm for coupling to an instrument.

FIG. 9 shows the distal end of a robotic arm 901 that forms part of a surgical robot. The arm may be similar to the robotic arm 203 shown in FIG. 2, for example. The arm comprises a mounting block 903 configured to attach to a surgical instrument 915. The surgical instrument is shown here detached from the robotic arm for clarity. It is also shown not to scale compared to the robotic arm. The surgical instrument comprises a housing 917 at its proximal end, and an end effector 919 at its distal end (shown here as a pair of grippers). An elongate shaft 921 extends between the housing and end effector.

The mounting block 903 comprises a terminating face 907. The plane of the terminating face may be generally transverse to the longitudinal extent of the arm or mounting block. The terminating face may be the most distal point of the robotic arm.

It may define the end of the robotic arm. The mounting block further comprises a planar surface 913 that is extends along the longitudinal extent of the arm. The surface 913 may be generally transverse to the terminating face 907. Surface 913 may be configured to mate or connect with the instrument housing 917 attached to the proximal end of the instrument. The mounting block defines a channel, or valley 905. The channel has an opening, or mouth 923 at the terminal end of the robotic arm. The channel is of U-shaped cross-section. The channel is intended to receive the proximal end of the instrument. During use of the robot in a surgical procedure, the robotic arm is covered by a surgical drape. The covering of the drape sits over the mounting block and the channel. The drape operates to define a sterile boundary over the robotic arm.

The robotic arm comprises a drive assembly for supplying drive to the instrument through the drape. The drive assembly may be housed within the robotic arm. In this example the drive assembly comprises a carriage 909 protruding from a side wall of the channel. The carriage may be attached to a linear actuator (not shown) which can drive the carriage bi-directionally along the longitudinal extent of the arm as indicated by the arrows 911. The carriage may be configured to receive a lug positioned at the proximal end of the instrument as described with reference to FIG. 4. The lug may for example be positioned within the housing 917 so that when the housing is interfaced with the surface 913 of the mounting block the instrument lug can be received by the carriage of the drive assembly. When the lug is received by the carriage, linear motion of the carriage causes corresponding motion of the lug to transfer drive to the surgical instrument. The robotic arm may comprise a plurality of carriages (e.g. three) for supplying drive to the instrument to selectively actuate the instrument joints, as described above.

The guiding structure of the drape may be configured to attach to the mounting block of the robotic arm 903. When the guiding structure is attached to the mounting block the interface elements of the drape are positioned in proximity to the drive assembly interfaces. This assists a user in being able to connect the interface elements to the drive assembly.

Figure 10:
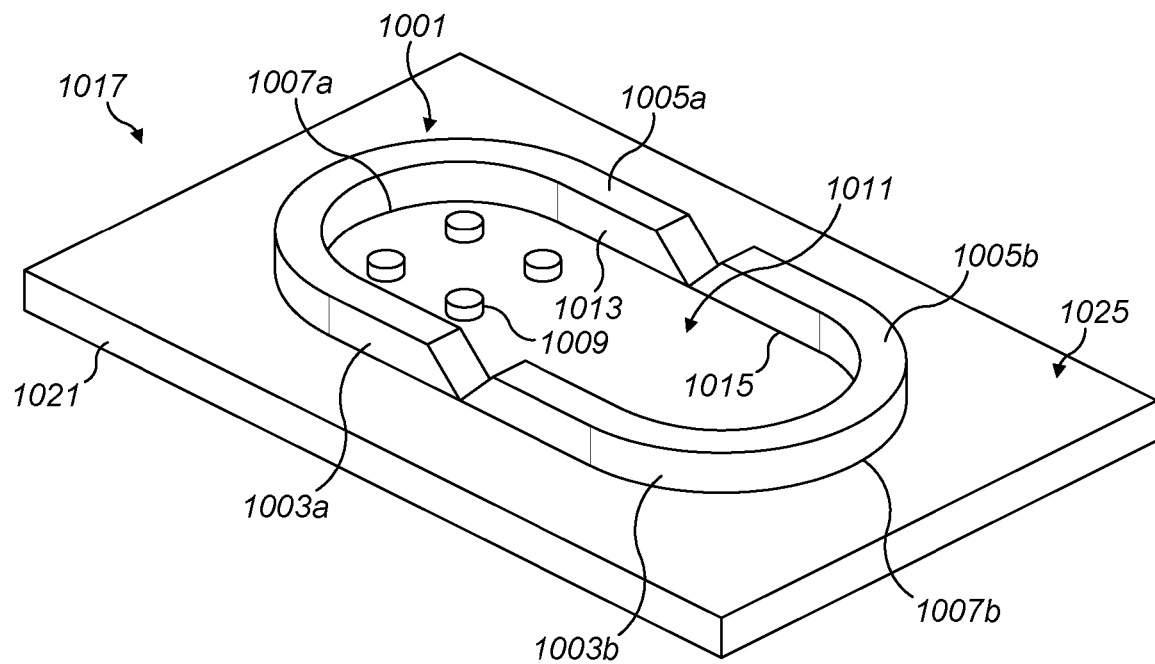
FIG. 10 shows a guiding structure attached to the covering of the drape in a storage configuration and an operative configuration.
Figure 10:
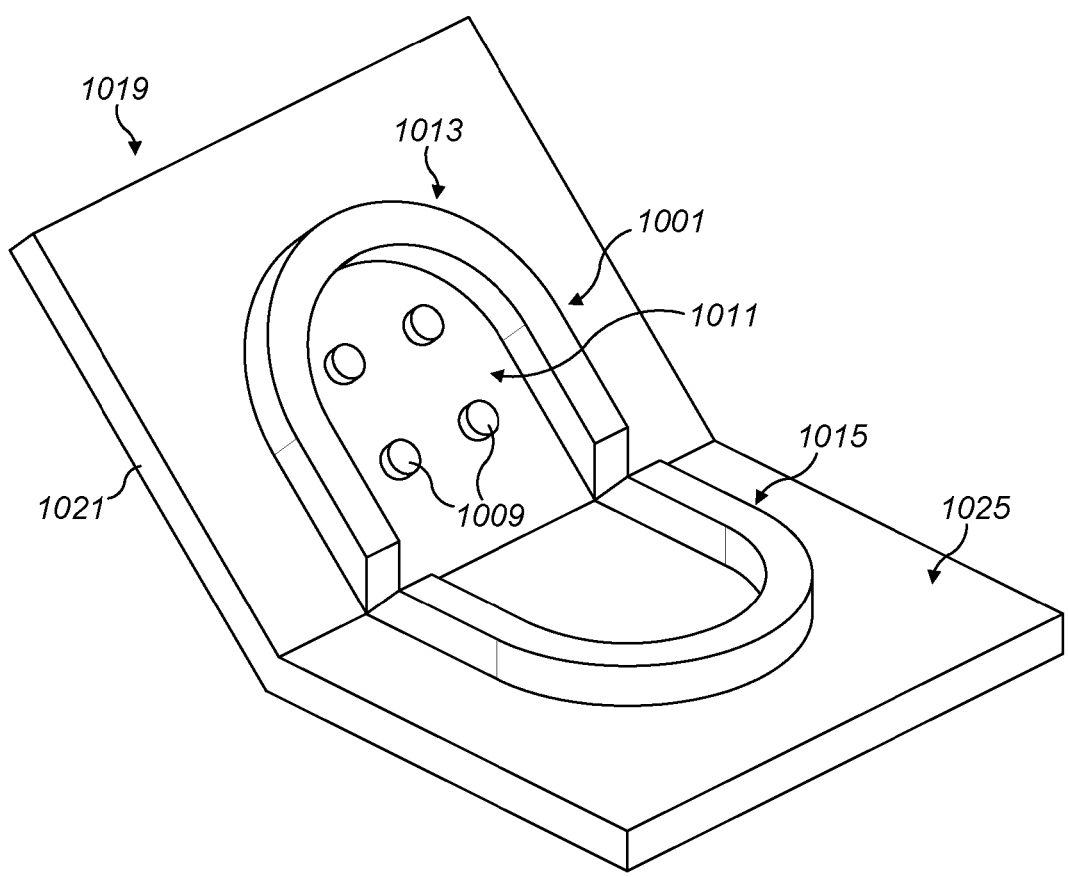

FIG. 10 shows an example of a guiding structure 1001 attached to the covering of the drape 1021 (of which only a portion is shown). The guiding structure is shown in both a storage configuration indicated generally at 1017, and an operative configuration indicated generally at 1019. The guiding structure is deformable between the storage and operative configurations. It may be manually deformable, e.g. by a nurse or a surgeon. The guiding structure may be placed into its storage configuration when the drape is to be stored (e.g. after manufacture, and/or prior to sale). The drape may be stored when it is not being used in a surgical procedure. It may be stored by operators of the surgical robot, or by the suppliers of the drape. In the storage configuration the guiding structure may be flat, or planar. This enables the drape to be flat-packed, or folded into a flat configuration. This is advantageous because it allows the drape to be more efficiently packaged. It may for example allow the drape to be packaged for sale with reduced amounts of packaging.

In its operative configuration the guiding structure is configured to attach to the robotic arm to position the interface elements of the drape with respect to the interfaces of the drive assembly for engagement therewith. In its operative configuration the guiding structure may be in a folded arrangement, as shown at 1019. This may assist in securely enveloping the drape over the robotic arm, as will be described in more detail below.

The guiding structure comprises a first segment 1013 and a second segment 1015. The first and second segments are articulated with respect to each other for deforming the structure between its storage and operative configurations. The first and second segments may be hingedly or pivotally connected to each other, for example. When the structure 1001 is in its storage configuration, the first and second segments are co-planar. This results in the guiding structure being flat, or planar. Planar may mean that the angle between the two segments is less than, e.g. 15 degrees, or 10 degrees, or 5 degrees etc. The guiding structure may exhibit a small degree of curvature, or deflection when in its storage configuration. When the structure 1001 is in its operative configuration, the first and second segments do not occupy the same plane and are not parallel with respect to each other. The angle between the first and second segments may for example be greater than 45 degrees. It may be greater than 60 degrees. In this example the first and segments are transverse, or perpendicular, to each other. Transverse may mean that the angle between the two segments is greater than, e.g. 70 degrees, 80 degrees or 85 degrees.

Each of the first and second segments has a perimeter defining an outer sidewall denoted $1003_a$ and $1003_b$ respectively. The first segment further comprises two opposing surfaces $1005_a$ and $1007_a$ and the second segment further comprises two opposing surfaces $1005_b$ and $1007_b$.

The guiding structure may be attached to the covering 1021 so that the structure protrudes from a single surface or side of the covering. The structure may be attached to the side, or surface, of the covering that faces the robotic arm. That is, it may be attached to the surface of the covering that interfaces with the non-sterile environment. This surface is indicated at 1025. The structure may be attached to the covering in a number of ways, e.g. it may be clipped, moulded, adhered, thermoformed or heat sealed thereon. The guiding structure may be attached to the covering during manufacture of the drape. It may be attached before or after the interface elements are attached.

The structure 1001 is attached to the covering to form a closed loop structure. That is, the guiding structure is shaped as a closed loop. The loop may be non-planar (e.g. when the structure is in its operative configuration). The guiding structure may be shaped as a ring, or annulus, when in its storage configuration. It may be in the shape of a lozenge.

The guiding structure encircles, or fences, interface elements 1009. Thus the interface elements 1009 are positioned within the bounds defined by the structure. It further encircles, or circumscribes, material of the covering (in this case it encircles an area or subsection of covering denoted by 1011). That is, a portion of the covering is positioned within the bounds defined by the structure. The portion is interior of the closed loop formed by the structure. The structure therefore delineates a subsection of the covering 1011 that has attached thereto the interface elements.

The encompassed interface elements may be attached to the covering by one or more pockets as shown in FIGS. 7 and 8. In this case the guiding structure encompasses, or encircles the one or more pockets (and hence the interface elements). The guiding structure subtends a portion or subsection of the covering that comprises the one or more pockets. The interface elements (and pockets, if present) are positioned interiorly of the ringed structure when viewed in plan in its storage configuration.

When in its operative configuration the guiding structure 1001 is configured to locate the interface elements 1009 relative to the drive-assembly interfaces that form part of the robotic arm drive assembly. To do this, the guiding structure is configured to attach to the robotic arm to position the interface elements with respect to the drive-assembly interfaces. The first and second segments of the guiding structure 1001 can both connect to the mounting block of the instrument arm. The two segments may connect to respective surfaces of the robotic arm mounting block (e.g. surfaces 907 and 913).

Figure 11:
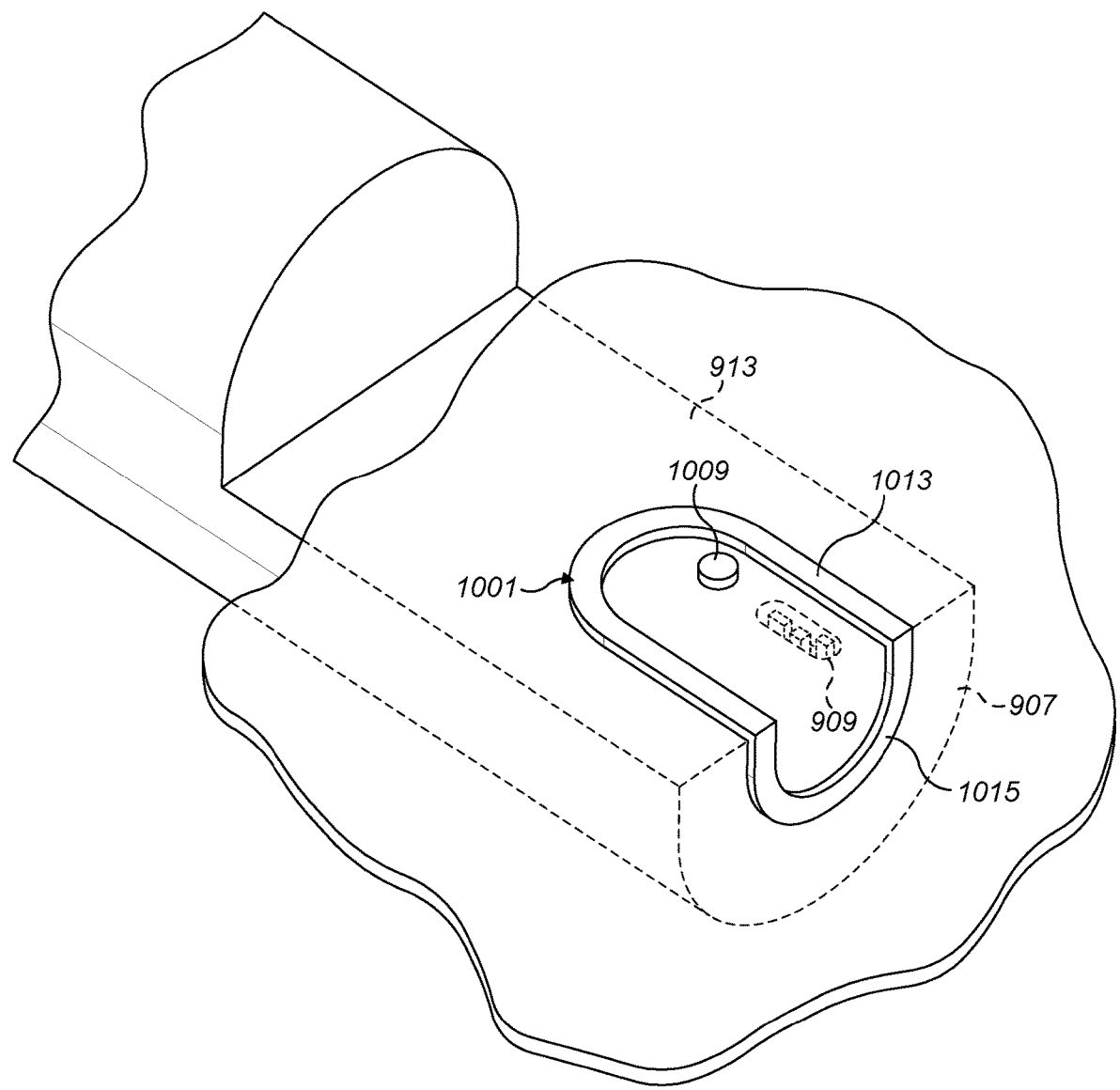
FIG. 11 shows a distal end of the robotic arm with the guiding structure attached.

FIG. 11 shows an example of how guiding structure 1001 can attach to the robotic arm 901. The mounting block of the robotic arm is shown in dashed lines to indicate that it is being covered by the drape (of which only a portion is shown for clarity). Similarly, only a single interface element of the drape is shown here for illustration. It can be seen that when the guiding structure is attached to the robotic arm, the interface element is positioned in proximity to the carriage 909 of the robotic arm drive assembly. A user can then engage the interface element with the robotic arm drive assembly by manoeuvring the interface element into place. This may be permitted by the flexibility of the drape covering, as discussed above.

The first segment 1013 is attached to surface 913 and the second segment 1015 is attached to the surface 907. The first and second segments may be hooked into position on the robotic arm. Alternatively they may be push-fitted, snap-fitted or clipped into position on the robotic arm. The structure may connect to the robotic arm via the surfaces $1005_{a,b}$. Surfaces $1005_{a,b}$ may therefore be referred to as robotic-arm-interface surfaces. For example, surfaces $1005_{a,b}$ may comprise surface features (e.g. ridges and/or lugs) that are configured to engage complementary features on surfaces 907 and 913 of the robotic arm (e.g. grooves). Alternatively the surfaces $1005_{a,b}$ may comprise grooves or recesses configured to engage with ridges/lugs on the mounting block 903.

The guiding structure may alternatively be configured to slidably engage the robotic arm. The guiding structure may be configured so that one of the first and second segments is configured to slidably engage a complementary surface on the arm. The other of the first and second segments may be push-fitted or clipped to the robotic arm. For example the first segment may be configured to slidably engage a groove that extends along the perimeter of the channel 905 (indicated at 925 in FIG. 9). The groove may be positioned in the sidewall of the channel. It may extend in a direction parallel to the surface 913 of the mounting block.

The guiding structure may be resiliently deformable when in its operative configuration so that the shape defined by its perimeter is deformable. The structure may be deformable between a compressed configuration in which the structure can slidably engage the groove, and an expanded configuration in which the structure cannot engage the groove. An expanded configuration may be one in which the diameter of the structure is greater than the width of the channel 905. The structure may be biased to its expanded configuration. Either one or both of the first and second segments can be resiliently deformable.

To slidably engage structure 1001 with the robotic arm, a user may squeeze together opposing arms of the first segment 1013 to deform the first segment to a compressed configuration in which the first segment can fit within the groove 925. The first segment can then be slotted within the groove. Once the structure is fitted within the groove, the resilient bias towards the expanded configuration holds the structure securely within the groove.

Figure 12:
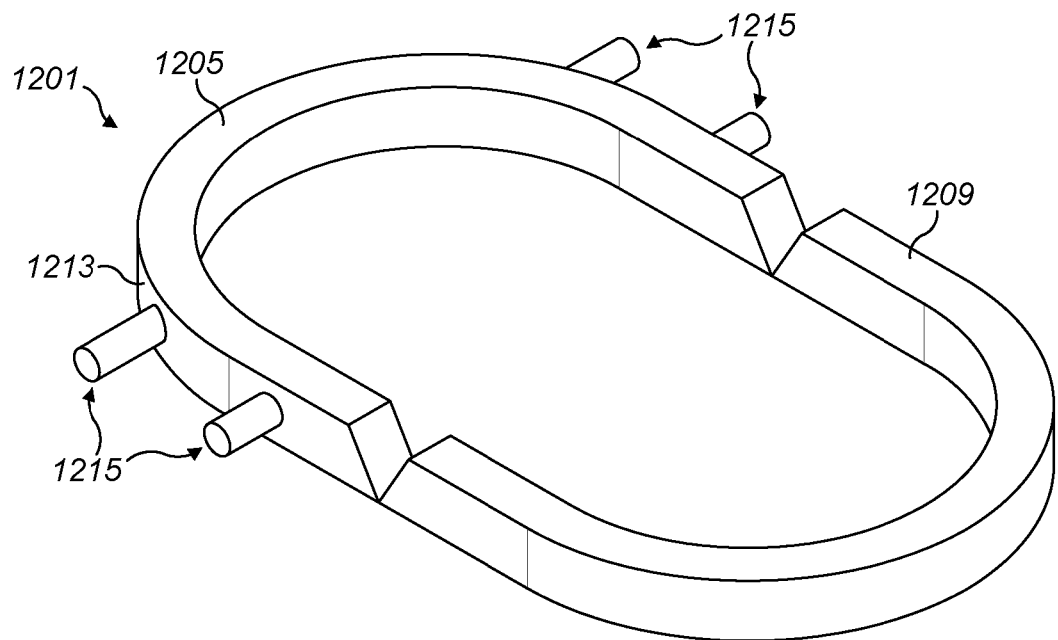
FIG. 12 shows examples of guiding structures with surface features for slidably engaging a robotic arm.
Figure 12:
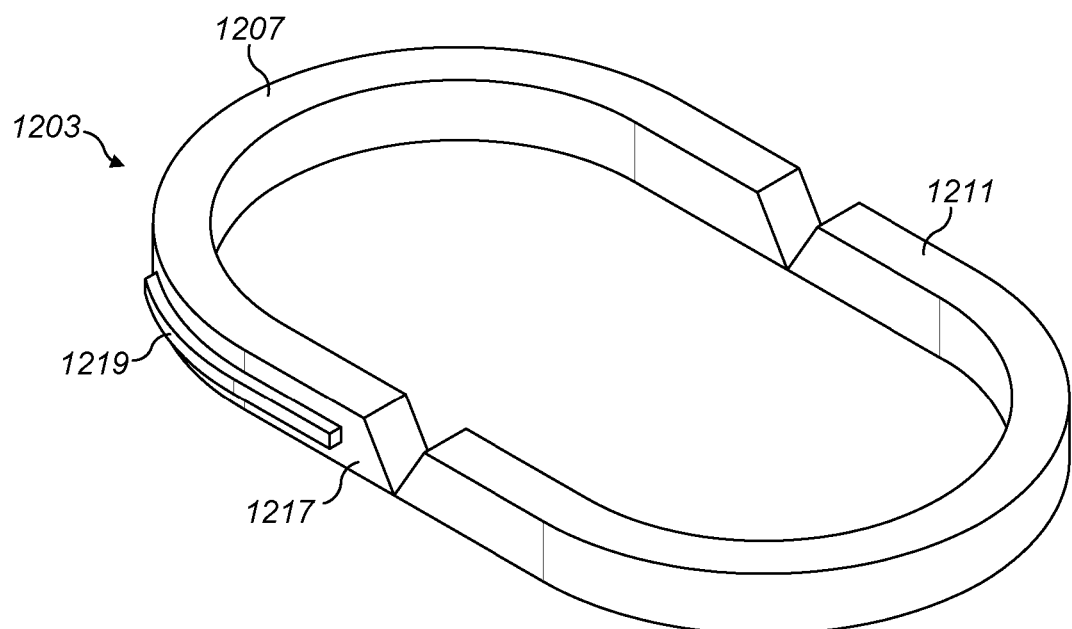

The guiding structure may comprise surface features that protrude from the outer sidewall of the first segment that are configured to slidably engage the groove. Examples of such surface features are shown in FIG. 12. Each of the guiding structures 1201 and 1203 comprise first segments (denoted 1205, 1207 respectively) and second segments (denoted 1209 and 1211 respectively). The structures are shown in their storage configuration. In these figures the drape covering has been omitted for clarity.

The outer sidewall 1213 of first segment 1205 has surface features in the form of a plurality of lugs 1215. The lugs extend in a direction transverse to the outer sidewall.

When the guiding structure is attached to the robotic arm the lugs are received within a groove located on the robotic arm (e.g. groove 925). The lugs may act as guide pins to assist the user in correctly attaching the structure to the robotic arm.

The outer sidewall 1217 of first segment 1207 has surface features in the form of a rib 1219. Rib 1219 extends circumferentially around the outer sidewall. When the guiding structure is attached to the robotic arm, the rib is received within a groove located on the robotic arm (e.g. groove 925). The guiding structure may alternatively comprise a plurality of ribs configured to engage respective grooves on the robotic arm.

The guiding structure may alternatively be configured so that the second segment is configured to slidably engage a groove that extends circumferentially along the channel (indicated at 927 in FIG. 9). The groove may be positioned in proximity to the mouth of the channel. It may extend in a direction parallel to the terminating surface 907. In this case the first segment may be configured to push-fit or clip onto the robotic arm. The second segment may as such comprise surface features protruding from its outer sidewall 1003*b*. These surface features may be in the form of lugs, or ribs, as discussed above with reference to FIG. 12. The guiding structure may alternatively comprise surface features on its sidewall in the form of grooves, or recesses that are configured to engage projections protruding into the channel 905.

In the example above, each of the first and second segments are configured to engage a respective surface of the robotic arm. Having the guiding structure engage multiple surfaces of the robotic arm is advantageous because it enables the drape to more securely envelope the robotic arm. For guiding structure 1001, the first segment attaches to the robotic arm to assist in enabling a user to more easily engage the interfacing elements of the drape with the drive assembly. The second segment 1015 attaches to the terminating face of the robotic arm 907 (or sits within groove 927) to assist in manipulating the drape to envelop the arm. Although the drape could be manipulated over the terminal portion of the robotic arm without attachment via the second segment, such a drape may be less securely held to the robotic arm.

The first and second segments of the guiding structure may be configured to interlock, or connect together when the structure is in its operative configuration. The first and second segments may be configured to clip together to securely hold the guiding structure in its operative configuration. An example of how the first and second segments may lock together is shown in FIG. 13.

Figure 13:
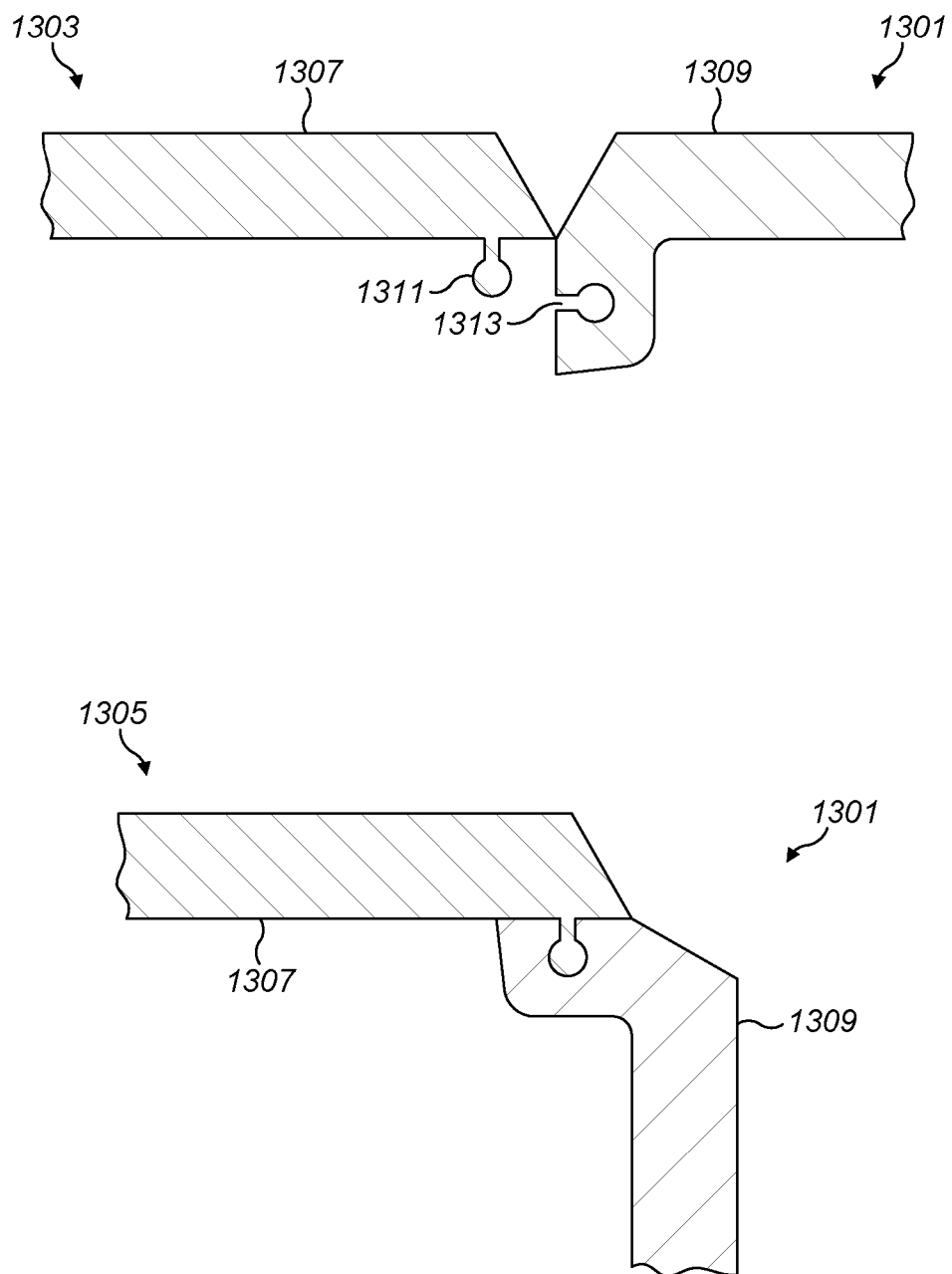
FIG. 13 shows a portion of a guiding structure in a storage and operative configuration that comprises interlocking interfaces to secure the structure in its operative configuration.

FIG. 13 shows a side-view of guiding structure 1301 in its storage configuration, indicated at 1303, and its operative configuration, indicated at 1305. Only a portion of the structure centered on the pivotal connection between the first and second segments (1307 and 1309 respectively) is shown. The remainder of the guiding structure and the drape has been omitted for clarity.

The first and second segments each comprise an interlocking interface indicated at 1311 and 1313 respectively. The interlocking interfaces are configured to engage each other when the guiding structure is in its operative configuration to secure the first and second elements together. The interlocking interfaces do not engage each other when the guiding structure is in its storage configuration. The interlocking interfaces may be transverse to each other when the structure is in its storage configuration.

In this example the interlocking interfaces are configured to push-fit, or snap-fit together. The interlocking interface 1311 comprises a projection in the form of a mushroom head that is configured to interlock, or mate, with a recess that forms part of the interlocking interface 1313. It will be appreciated that the projections shown here are merely for example and the interlocking interfaces may be any suitable complementary surfaces capable of locking together.

The interlocking interfaces may be configured to releasably lock. That is, the first and second segments may be deformable from the operative configuration to the storage configuration upon a suitable manual force. A suitable manual force may be one which is low enough to enable the interfaces to be unlocked manually by a user, but high enough that the interfaces will not unlock unintentionally, for example if a user were to accidentally knock the guiding structure during a surgical procedure.

Although only one pair of interlocking interfaces are shown in FIG. 13, it will be appreciated that the guiding structure may comprise a second pair of interlocking interfaces on an opposing side of the structure. The first and second pair of interlocking interfaces may lie on or proximal to the pivotal axis about which the structure pivots when being deformed between its storage and operative configurations.

In an alternative example, the guiding structure may be configured so that when in its storage configuration the first and second segments are parallel but not planar. The first and second segments may for example be in a stacked arrangement. That is, one of the first and second segments is folded back onto the other of the first and second segments when the structure is in the stored configuration. The first and second segments may therefore be congruent when the structure is in its storage configuration. This reduces the surface area of the guiding structure in its storage configuration compared to the example in which the first and second segments are parallel and planar, which may make the drape for easily folded for storage and packing.

In the examples described above the guiding structure comprises first and second segments pivotable relative to each other. The guiding structure may alternatively comprise a single segment that forms a closed loop structure. The segment may be elastic, or flexible, to permit the structure to be deformed between its storage and operative configurations. The structure may be resiliently deformable between its storage and operative configurations so that the structure is biased towards its storage configuration (in which the segment is planar, or flat, or level). Such a guiding structure may comprise surface features for attachment to the robotic arm as in the examples described above. Further, although in the examples described above the guiding structure encompasses a plurality of drape interface elements, it will be appreciated that the guiding structure could equally well be used to locate a single interface element relative to the drive assembly. Thus the guiding structure may encompass or surround a single interface element.

Figure 14:
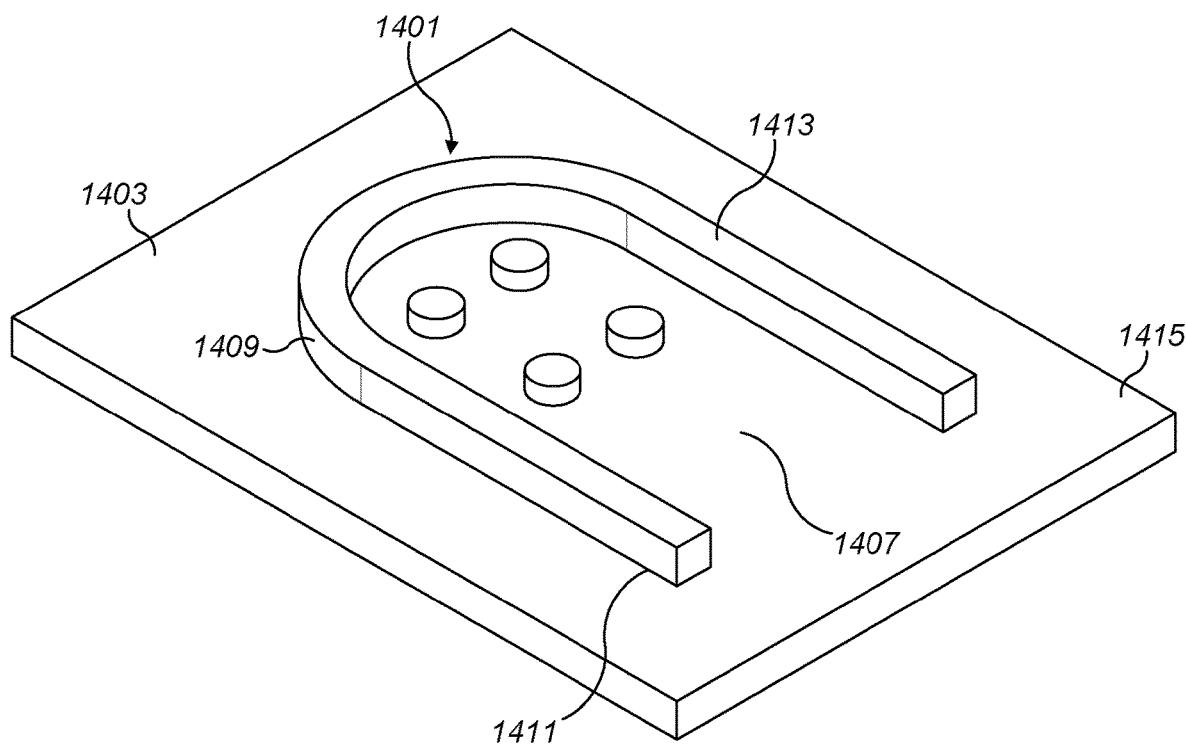
FIG. 14 shows an alternative example of a guiding structure.

FIG. 14 shows an alternative example of a guiding structure 1401. The guiding structure 1401 is a hooped structure attached to the covering of the drape 1403. Only a portion of the covering is shown for clarity. The guiding structure is shaped as an open loop. That is, the structure does not form a closed loop as in the examples described above. The structure may be an arced, or crescent-shaped structure. It may be shaped as a semicircle. The structure may resemble the first segment of the guiding structures above.

The hooped structure has a perimeter that defines an outer sidewall 1409. The structure further comprises opposing surfaces 1411 and 1413. It may be attached to the covering via one of the opposing surfaces only (in this example surface 1411). It may be attached to the side of the covering 1415 that interfaces with the non-sterile environment. The other opposing surface (1413) may be used to attach the structure to the robotic arm. Surface 1413 may as such be referred to as a robotic-arm-interface surface.

The hooped structure encompasses material of the covering and a plurality of interface elements 1405 that are fixed to the covering. That is, the interface elements of the drape are positioned on the covering within the bounds of the hooped structure. The interface elements are interior of the hooped structure, e.g. when the structure is viewed in plan. The hooped structure thus circumscribes a subsection or portion of the drape covering 1407 that contains the interface elements. The hooped structure may subtend a section of the covering 1407 that has affixed thereto the plurality of interface elements. The hooped structure may encompass material of the covering that comprises one or more pockets as described above with reference to FIG. 8. Thus the hooped structure may subtend material of the covering that forms the one or more pockets.

The guiding structure is positioned relative to the plurality of interface elements so that when the structure is attached to the robotic arm the plurality of interface elements are positioned with respect to the interfaces of the drive assembly for engagement therewith. Thus, when the guiding structure is attached to the robotic arm the interface elements are located, or positioned, in proximity to the drive-assembly interfaces. The guiding structure may be configured to attach to the robotic arm according to any of the examples described with reference to FIGS. 11 to 12. For example the structure may slidably engage a complementary surface positioned on the robotic arm (e.g. groove 925 or 927). In this case the outer sidewall 1409 may have surface features configured to engage a complementary surface on the robotic arm. Alternatively the structure may comprise surface features on the robotic-arm-interface surface 1413 that enable the structure to be push-fitted, snap-fitted or clipped onto the robotic arm.

Although shown as an open looped structure, the guiding structure 1401 may alternatively be shaped as a closed loop. The structure may therefore be in the form of an annulus, or ring. It may be rigid. That is, it may have a single configuration and not be deformable between storage and operative configurations. The guiding structure may alternatively encompass a single interface element and material of the covering.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical robotic drape configured to envelope a portion of a surgical robot to define a sterile boundary thereover, the surgical robot comprising an instrument comprising three joints and an end effector at the distal end of the instrument, and a robotic arm comprising a drive assembly configured to provide linear mechanical drive so as to selectively actuate the three joints, a proximal end of the instrument being located at the distal end of the robotic arm, and the proximal end of the instrument opposing the distal end of the robotic arm in a first direction, the proximal end of the instrument having a plurality of instrument interfaces, and the drive assembly having a plurality of drive assembly interfaces configured to couple linear mechanical drive from the drive assembly to the instrument, the drape comprising:
 a plurality of interface elements, each of the plurality of interface elements configured to engage with both one of the plurality of drive assembly interfaces within the sterile boundary of the drape and one of the plurality of instrument interfaces outside the sterile boundary of the drape to couple the drive assembly to the instrument to thereby transfer linear mechanical drive provided by the drive assembly linearly through a material of the drape to selectively actuate a respective joint of the instrument, the plurality of interface elements being attached to the material of the drape in a spatial arrangement so that each of the plurality of interface elements is separated from each of other of the plurality of interface elements by the material of the drape, the material of the drape is deformable, and
 a planar extent of the drape extending in a second direction, perpendicular to the first direction;
 wherein a portion of the material of the drape separating the plurality of interface elements is configured to be deformed to change the spatial arrangement of the interface elements by the drive assembly, the drive assembly is configured to provide linear mechanical drive, for selectively actuating the three joints, in the second direction, parallel to the planar extent of the drape, between the distal end of the robotic arm and the proximal end of the instrument.

2. A surgical robotic drape as claimed in claim 1, wherein the material of the drape is flexible such that each of the plurality of interface elements is not spatially fixed with respect to each of the other of the plurality of interface elements.

3. A surgical robotic drape as claimed in claim 1, wherein the material of the drape is flexible thereby permitting the spatial arrangement of the interface elements to be adjusted.

4. A surgical robotic drape as claimed in claim 1, wherein the material of the drape is flexible thereby permitting spatial movement of each of the plurality of interface elements relative to one another to alter the spatial arrangement thereof.

5. A surgical robotic drape as claimed in claim 1, wherein the spatial arrangement of the interface elements with respect to each other is dependent on the configuration of the drape.

6. A surgical robotic drape as claimed in claim 1, wherein each interface element comprises a first interfacing surface to engage one of the plurality of drive assembly interfaces and a second interfacing surface to engage one of the plurality of instrument interfaces.

7. A surgical robotic drape as claimed in claim 6, wherein each of the interface elements is configured to releasably engage with one of the plurality of drive assembly interfaces and one of the plurality of instrument interfaces, and each interface element is configured so that its first interfacing surface is configured to engage a complementary surface of the one of the plurality of drive assembly interfaces and its second interfacing surface is configured to engage a complementary surface of the one of the plurality of instrument interfaces so that it requires a greater force to disengage the interface element from the one of the plurality of drive assembly interfaces than from the one of the plurality of instrument interfaces.

8. A surgical robotic drape as claimed in claim 6, wherein at least one of the interface elements is configured so that its first interfacing surface comprises surface features configured to engage a complementary surface of one of the plurality of drive assembly interfaces.

9. A surgical robotic drape as claimed in claim 6, wherein at least one of the interface elements is configured so that its second interfacing surface comprises surface features configured to engage a complementary surface of one of the plurality of instrument interfaces.

10. A surgical robotic drape as claimed in claim 6, wherein at least one of the interface elements is configured so that its first interfacing surface comprises surface features configured to engage a complementary surface of a one of the plurality of drive assembly interfaces and its second interfacing surface comprises surface features configured to engage a complementary surface of one of the plurality of instrument interfaces.

11. A surgical robotic drape as claimed in claim 8, wherein the surface features of the first interfacing surface are configured to mate with a complementary surface of one of the plurality of drive assembly interfaces to thereby secure the drape to the robotic arm.

12. A surgical robotic drape as claimed in claim 1, wherein each interface element is mounted directly to the drape.

13. A surgical robotic drape as claimed in claim 1, wherein the plurality of interface elements comprise: a first subset of interface elements each configured to engage one of the plurality of drive assembly interfaces and one of the plurality of instrument interfaces to thereby transfer mechanical drive through the drape to actuate a first joint of the instrument; a second subset of interface elements each configured to engage another of the plurality of drive assembly interfaces and another of the plurality of instrument interfaces to thereby transfer mechanical drive through the drape to actuate a second joint of the instrument; a third subset of interface elements each configured to engage a further one of the plurality of drive assembly interfaces and a further one of the plurality of instrument interfaces to thereby transfer mechanical drive through the drape to actuate a third joint of the instrument.

14. A surgical robotic drape as claimed in claim 13, wherein the drape comprises a first, a second, and a third pocket each formed from the drape, each pocket configured to receive a respective lug protruding from a proximal portion of the instrument, the drape being configured so that the first subset of interface elements are attached to the first pocket, the second subset of interface elements are attached to the second pocket, and the third subset of interface elements are attached to the third pocket.

15. A surgical robotic drape as claimed in claim 14, wherein the first subset of interface elements are configured to engage respective instrument interfaces located on a first lug, the second subset of interface elements are configured to engage respective instrument interfaces located on a second lug and the third subset of interface elements are configured to engage respective instrument interfaces located on a third lug.

16. A surgical robotic drape as claimed in claim 1, wherein the drape comprises a first, a second, and a third pocket each formed from the drape, each pocket configured to receive a respective lug protruding from a proximal portion of the instrument, each pocket having at least one interface element attached thereto configured to engage a one of the plurality of drive assembly interfaces and one of the plurality of instrument interfaces located on the respective lug to thereby transfer mechanical drive through the drape to actuate a respective joint of the instrument.

17. A surgical robotic system configured to perform robotic surgery, the robotic system comprising:
 a surgical robot comprising an instrument comprising three joints, and a robotic arm comprising a drive assembly configured to provide linear mechanical drive so as to selectively actuate the three joints, a proximal end of the instrument being located at a distal end of the robotic arm, and the proximal end of the instrument opposing the distal end of the robotic arm in a first direction, and the proximal end of the instrument having a plurality of instrument interfaces and the drive assembly having a plurality of drive assembly interfaces configured to couple linear mechanical drive from the drive assembly to the instrument; and
 a surgical robotic drape configured to envelope a portion of the surgical robot to define a sterile boundary thereover, the surgical robotic drape comprising:
  a plurality of interface elements, each of the plurality of interface elements engaging with both one of the plurality of drive assembly interfaces within the sterile boundary of the drape and one of the plurality of instrument interfaces outside the sterile boundary of the drape to couple the drive assembly to the instrument to thereby transfer linear mechanical drive provided by the drive assembly linearly through material of the drape to selectively actuate a respective joint of the instrument, the plurality of interface elements being attached to the material of the drape in a spatial arrangement so that each of the plurality of interface elements is separated from each of other of the plurality of interface elements by the material of the drape; and a planar extent of the drape extending in a second direction, perpendicular to the first direction;

wherein the drive assembly is configured to provide linear mechanical drive, for selectively actuating the three joints, in the second direction, parallel to the planar extent of the drape, between the distal end of the robotic arm and the proximal end of the instrument.

18. The surgical robotic drape of claim 1, wherein the plurality of interface elements are studs mounted to the surgical robotic drape.

19. The surgical robotic drape of claim 1, comprising a pocket formed by the material of the drape, wherein an interface element of the plurality of interface elements is a stud mounted to the pocket.

20. A surgical robotic drape configured to envelope a portion of a surgical robot to define a sterile boundary thereover, the drape comprising:

a plurality of interface elements, each of the plurality of interface elements configured to engage with both one of a plurality of drive assembly interfaces of the surgical robot within the sterile boundary of the drape and one of a plurality of instrument interfaces of an instrument outside the sterile boundary of the drape to couple a surgical robot drive assembly to the instrument to thereby transfer mechanical drive provided by the drive assembly through a material of the drape to selectively actuate a respective joint of the instrument, the plurality of interface elements being attached to the material of the drape in a spatial arrangement so that each interface element of the plurality of interface elements is separated from each of the other of the plurality of interface elements by the material of the drape, the material of the drape is deformable, wherein a portion of the material of the drape separating the plurality of interface elements is configured to be deformed by motion of at least one interface element of the plurality of interface elements to change the spatial arrangement of the interface elements as a drive assembly of the surgical robot urges motion of at least one interface element of the plurality of interface elements.

* * * * *